(12) United States Patent
Tanaka et al.

(10) Patent No.: US 11,324,704 B2
(45) Date of Patent: May 10, 2022

(54) SUSTAINED DRUG RELEASE SHEET FOR TREATING NERVE INJURY

(71) Applicants: OSAKA UNIVERSITY, Suita (JP); NATIONAL INSTITUTE FOR MATERIALS SCIENCE, Tsukuba (JP); NIPPON ZOKI PHARMACEUTICAL CO., LTD., Osaka (JP)

(72) Inventors: Hiroyuki Tanaka, Suita (JP); Kiyoshi Okada, Suita (JP); Hideki Yoshikawa, Suita (JP); Koji Suzuki, Suita (JP); Mitsuhiro Ebara, Tsukuba (JP)

(73) Assignees: OSAKA UNIVERSITY, Osaka (JP); NATIONAL INSTITUTE FOR MATERIALS SCIENCE, Tsukuba (JP); NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/082,594

(22) PCT Filed: Mar. 6, 2017

(86) PCT No.: PCT/JP2017/008730
§ 371 (c)(1),
(2) Date: Sep. 6, 2018

(87) PCT Pub. No.: WO2017/154822
PCT Pub. Date: Sep. 14, 2017

(65) Prior Publication Data
US 2019/0083415 A1    Mar. 21, 2019

(30) Foreign Application Priority Data

Mar. 7, 2016 (JP) .................................. 2016-043873
Jan. 20, 2017 (JP) .................................. 2017-008913
Feb. 28, 2017 (JP) .................................. 2017-037270

(51) Int. Cl.
| A61K 9/70 | (2006.01) |
| A61K 47/34 | (2017.01) |
| A61K 47/36 | (2006.01) |
| A61K 31/714 | (2006.01) |
| A61K 35/36 | (2015.01) |
| A61K 45/00 | (2006.01) |
| A61K 38/18 | (2006.01) |
| A61P 25/02 | (2006.01) |
| A61K 47/32 | (2006.01) |

(52) U.S. Cl.
CPC .............. *A61K 9/7007* (2013.01); *A61K 9/70* (2013.01); *A61K 31/714* (2013.01); *A61K 35/36* (2013.01); *A61K 38/18* (2013.01); *A61K 38/185* (2013.01); *A61K 45/00* (2013.01); *A61K 47/32* (2013.01); *A61K 47/34* (2013.01); *A61K 47/36* (2013.01); *A61P 25/02* (2018.01)

(58) Field of Classification Search
CPC combination set(s) only.
See application file for complete search history.

(56) References Cited

U.S. PATENT DOCUMENTS

| 6,110,472 A | * | 8/2000 | Levere .................... A61K 8/19 |
| | | | 424/401 |
| 2005/0169967 A1 | | 8/2005 | Gilchrist et al. |
| 2008/0241267 A1 | | 10/2008 | Verrijk |
| 2011/0129510 A1 | | 6/2011 | Liebmann et al. |
| 2012/0220962 A1 | * | 8/2012 | Hsu ...................... A61K 9/0014 |
| | | | 604/307 |
| 2013/0122512 A1 | | 5/2013 | Mutoh et al. |
| 2014/0141050 A1 | * | 5/2014 | Ploger .................... A61F 13/00 |
| | | | 424/402 |
| 2015/0037375 A1 | | 2/2015 | Grinstaff et al. |
| 2015/0151020 A1 | * | 6/2015 | Kageyama ........... A61K 38/363 |
| | | | 424/445 |
| 2015/0352209 A1 | | 12/2015 | Ebara et al. |

FOREIGN PATENT DOCUMENTS

| CN | 102525689 B | | 6/2015 | |
| JP | S60-255726 A | | 12/1985 | |
| JP | 07241433 | * | 9/1995 | ............ B01D 53/34 |
| JP | 2005-220070 A | | 8/2005 | |
| JP | 2005-528145 A | | 9/2005 | |
| JP | 2007-236551 A | | 9/2007 | |
| JP | 2007236551 | * | 9/2007 | ............ A61L 27/00 |
| JP | 2007-529508 A | | 10/2007 | |
| JP | 2011-530661 A | | 12/2011 | |
| JP | 2014-177490 A | | 9/2014 | |
| JP | 2014-522918 | * | 9/2014 | ............ A61L 15/32 |
| JP | 2014-522918 A | | 9/2014 | |
| WO | 2007/089259 A1 | | 8/2007 | |
| WO | 2011/162317 A1 | | 12/2011 | |
| WO | 2013/013038 A2 | | 1/2013 | |
| WO | 2014/109379 A1 | | 7/2014 | |

OTHER PUBLICATIONS

JP07241433 A, Hasegawa, Koyama T, published Sep. 19, 1995. Abstract translation (Year: 1995).*

(Continued)

*Primary Examiner* — Audrea B Coniglio
(74) *Attorney, Agent, or Firm* — Oliff PLC

(57) ABSTRACT

Provided is a sustained release sheet that includes a drug for treating nerve injury, wherein the sheet is applied to a nerve injury site, can maintain a high concentration of the drug over a long period, and promotes nerve regeneration without stimulating the nerves, even when the sheet is implanted in the periphery of the nerve injury site. Also provided is a production method for the sheet. This sustained drug release sheet for treating nerve injury is a sheet comprising a non-woven fabric that is formed from nanofibers each containing a drug such as vitamin B12 and a biocompatible polymer such as a biodegradable aliphatic polyester, and is implanted in the periphery of the nerve injury site to promote nerve regeneration.

8 Claims, 17 Drawing Sheets

(56) References Cited

OTHER PUBLICATIONS

Sep. 11, 2018 International Preliminary Report on Patentablity issued in International Patent Application No. PCT/JP2017/008730.
Jul. 18, 2017 International Search Report issued in International Patent Application No. PCT/JP2017/008730.
Scalabrino et al.; "Subacute Combined Degeneration and Induction of Ornithine Decarboxylase in Spinal Cords of Totally Gastrectomized Rat"; Laboratory Investigation vol. 62. No. 3, pp. 297-304. 1990.
Okada et al.; "Methylcobalamin increases Erk1/2 and Akt activities through the methylation cycle and promotes nerve Yegeneration in a rat sciatic nerve injury model"; Experimental Neurology vol. 222, pp. 191-203, Jan. 4, 2010.
Suzuki et al.; "Electrospun nanofiber sheets incorporating methylcobalamin promote nerve regeneration and functional recovery in a rat sciatic nerve crush injury model"; Acta Biomaterialia (2017), doi: http:// dx.doi.org/10.1016/j.actbio.2017.02.004.
Sep. 10, 2019 Extended Search Report issued in European Patent Application No. 17763162.9.
Shim, Sun Woo et al., "Evaluation of Small Intestine Submucosa and Poly(Caprolactone-Co-Lactide) Conduits for Peripheral Nerve Regeneration", Tissue Engineering Part A, vol. 21, Nos. 5-6, (2015), pp. 1142-1151.
Okuzaki, H. et al. "Non-woven fabric of poly(N-isopropylacrylamide) nanofibers fabricated by electrospinning", Synthetic Metals, vol. 159, Issues 21-22, pp. 2273-2276, Nov. 2009.
Motoyoshi K. et al., "Restoring Nerve and Muscle Function with Local Application of bFGF", The Larynx Japan, vol. 23(2), pp. 62-65 (2011).
Dec. 22, 2021 Office Action issued in Chinese Patent Application No. 201780015992.7.
Dang, Dongxu et al. "Multifunctional Fluid Acupuncture Minimally Invasive Therapeutics," Beijing People's Army Medical Publishing House, 2nd Edition, Mar. 2012.
Han, Xiao et al. "Peking Union Clinical Medication Quick Reference Manual," Beijing: Peking Union Medical College Press, Sep. 2015.
Shao, Ying. "Higher Vocational Education 'Twelfth Five-Year Plan' Teaching Materials," Food Biochemistry, China Light Industry Press, Aug. 2015.
Jan. 28, 2022 Examination Report issued in Australian Patent Application No. 2017230387.

* cited by examiner

SUSTAINED DRUG RELEASE SHEET FOR TREATING NERVE INJURY

TECHNICAL FIELD

The present invention relates to a sustained drug release sheet for treating nerve injury (also simply referred to as "the present sheet", hereinbelow). More specifically, the present invention relates to: a sheet which contains a drug having a therapeutic effect on nerve injury and from which the drug can be released sustainably; a method for producing the sheet; and others.

BACKGROUND ART

Peripheral nerve injury is roughly classified into: discontinuity injury in which continuity is disrupted at an injured site; and continuity nerve injury in which continuity is retained at an injured site, such as entrapment neuropathy (e.g., carpal tunnel syndrome). As the method for treating discontinuity injury, direct suture, autologous nerve grafting or the like is selected. On the other hand, as the method for treating continuity nerve injury, neurolysis or a conservative treatment is selected. Heretofore, for a device having a regeneration effect on peripheral nerve injury, the development of artificial nerve conduits has been advanced. However, the artificial nerve conduits are those to be used only for discontinuity nerve injury. Furthermore, the artificial nerve conduits can just crosslink defects in an injured site and do not have an effect to enhance the regeneration of nerve axons. If a long period is required for the recovery of nerves after peripheral nerve injury, an irreversible change may occur in a muscle tissue. Therefore, to enhance the regeneration of nerve axons is a critical problem. Furthermore, as mentioned above, artificial nerve conduits can be applied only to nerve injury in which defects are present in an injured site, and there is not yet a device for continuity nerve injury with the incidence of a largest number of patients. In these situations, a tool which can be applied to both of continuity nerve injury and discontinuity nerve injury and is effective for the treatment of nerve injury has been demanded in clinical practice.

One of the drugs that can be contained in the present sheet is vitamin B12. Vitamin B12 is essential to normal functioning of nervous systems, and it is known that the insufficient amount of vitamin B12 causes systemic neuropathy called "subacute combined degeneration of the spinal cord" (Non-Patent Document 1). The present inventors have reported that the use of methylcobalamin at a concentration of 100 nM or more can promote the elongation of neurites and the survival of neurons, these effects can be mediated by a methylation cycle that is a reaction associated with methylation, methylcobalamin can increase the activities of Erk1/2 and Akt through the methylation cycle, and the continuous high-dose administration of methylcobalamin improves nerve regeneration and function recovery in a rat sciatic nerve injury model (Non-Patent Document 2).

Patent Document 1 discloses a biodegradable composite material which contains water-soluble glass fibers and a biocompatible binding material such as polycaprolactone and has a flexible sheet-like form so as to be implanted into a body. It is described that the biodegradable composite material having a flexible sheet-like form is wound around a tissue defect site upon use in order to accelerate the healing of the defect site, and is used for the prevention of the adhesion after a surgical operation. It is also described that the biodegradable composite material can be used as an alternative to a nerve graft, and therefore the biodegradable composite material is expected to be applied to a discontinuity nerve injury. However, the biodegradable composite material does not have an effect to enhance the regeneration of nerve axons.

As the drug that can be contained in the present sheet, an extract from inflamed skins of rabbits inoculated with vaccinia virus (also referred to as "the present extract", hereinbelow) or a fraction thereof can also be mentioned. With respect to the present extract or a preparation containing the present extract, very wide varieties of activities and effects thereof are known. However, a sheet for treating nerve injury which contains the present extract is not known yet.

As the drug that can be added to the present sheet, nerve growth factor (NGF), brain-derived neurotrophic factor (BDNF) and the like can also be mentioned. These substances are secretory proteins which belong to a neurotrophic factor family to which neurotrophin-3 (NT-3) and the like also belong, and which can be produced in various cells, including neurons and glial cells (e.g., a microglia, an astrocyte, an oligodendrocyte). A neurotrophin has an activity to maintain the survival of neurons, to enhance the elongation of neurites, to accelerate the synthesis of a neurotransmitter and the like. NGF can be synthesized and secreted in a target cell to which a neuron projects (e.g., a neuron, a muscle), can be taken through a TrkA receptor located at an axon terminal of a neuron, is delivered to a cell retrogradely and acts in the cell. NGF can act specifically on a sensory neuron (a dorsal root ganglion small cell) or a postganglionic sympathetic neuron in the peripheral nervous system, and can act specifically on a basal forebrain cholinergic neuron that projects to the cerebral cortex or the hippocampus in the central nervous system. It is known that BDNF is eccentrically located in the central nervous system such as mainly hippocampus and exhibits various physiological activities, including the survival/maintenance of nerve cells, the regulation of the forms of neurites, the functional regulation of synapse, and the regulation of neural plasticity, in nervous systems. However, sheets for treating nerve injury which contain these neurotrophins are unknown previously.

PRIOR ART DOCUMENTS

Patent Document

Patent Document 1: Japanese Patent Laid-Open No. 2005-528145

Non-Patent Documents

Non-Patent Document 1: Scalabrino et al., Lab. Invest., 62 (1990), 297-304
Non-Patent Document 2: Okada et al., Experimental Neurology, 222 (2010), 191-203

SUMMARY OF THE INVENTION

Problem to be Solved by the Invention

The present invention addresses the problem of providing a sustained drug release sheet for treating nerve injury which can keep the concentration of a drug in an injury site at a proper level for a long period and, when implanted into the periphery of a nerve injury site, can enhance the regeneration of nerves without applying stimuli that may adversely affect the nerves.

Means for Solving the Problems

In order to solve the problem, the present invention includes the following inventions. The more details of these inventions will be mentioned later.

[1] A sustained drug release sheet comprising a non-woven fabric that is formed from nanofibers each containing a drug for treating nerve injury and a biocompatible polymer.

[2] The sustained drug release sheet according to the above-mentioned item [1], wherein the drug is vitamin B12.

[3] The sustained drug release sheet according to the above-mentioned item [1], wherein the drug is an extract from inflamed skins of rabbits inoculated with vaccinia virus or a fraction thereof.

[4] The sustained drug release sheet according to the above-mentioned item [1], wherein the drug is a neurotrophin.

[5] The sustained drug release sheet according to the above-mentioned item [4], wherein the neurotrophin is NGF or BDNF.

[6] The sustained drug release sheet according to any one of the above-mentioned items [1] to [5], wherein the biocompatible polymer is a biodegradable aliphatic polyester or a polyacrylamide derivative.

[7] The sustained drug release sheet according to the above-mentioned item [6], wherein the biodegradable aliphatic polyester is selected from the group consisting of polycaprolactone or a copolymer thereof, polylactic acid or a copolymer thereof, polyglycolic acid or a copolymer thereof, and mixtures of these components.

[8] The sustained drug release sheet according to the above-mentioned item [6], wherein the polyacrylamide derivative is selected from the group consisting of poly(N-isopropylacrylamide) or a copolymer thereof, poly(2-hydroxyethylmethacrylamide) or a copolymer thereof, a copolymer of N-isopropylacrylamide and 2-hydroxyethylmethacrylamide, and mixtures of these components.

[9] The sustained drug release sheet according to any one of the above-mentioned items [1] to [8], wherein the Young's modulus of the sheet is 100 kPa to 100 MPa.

[10] The sustained drug release sheet according to any one of the above-mentioned items [1] to [9], wherein the weight of the sheet is 1 to 100 mg/cm$^2$.

[11] A sustained drug release sheet which comprises a non-woven fabric formed from nanofibers containing a drug and a biocompatible polymer, and has a Young's modulus of 100 kPa to 100 MPa and a weight of 1 to 100 mg/cm$^2$.

[12] The sustained drug release sheet according to the above-mentioned item [11], wherein the drug is vitamin B12.

[13] The sustained drug release sheet according to the above-mentioned item [11], wherein the drug is an extract from inflamed skins of rabbits inoculated with vaccinia virus or a fraction thereof.

[14] The sustained drug release sheet according to the above-mentioned item [11], wherein the drug is a neurotrophin.

[15] The sustained drug release sheet according to the above-mentioned item [14], wherein the neurotrophin is NGF or BDNF.

[16] The sustained drug release sheet according to any one of the above-mentioned items [11] to [15], wherein the biocompatible polymer is a biodegradable aliphatic polyester or a polyacrylamide derivative.

[17] The sustained drug release sheet according to the above-mentioned item [16], wherein the biodegradable aliphatic polyester is selected from the group consisting of polycaprolactone or a copolymer thereof, polylactic acid or a copolymer thereof, polyglycolic acid or a copolymer thereof, and mixtures of these components.

[18] The sustained drug release sheet according to the above-mentioned item [16], wherein the polyacrylamide derivative is selected from the group consisting of poly(N-isopropylacrylamide) or a copolymer thereof, poly(2-hydroxyethylmethacrylamide) or a copolymer thereof, a copolymer of N-isopropylacrylamide and 2-hydroxyethylmethacrylamide, and mixtures of these components.

[19] The sustained drug release sheet according to any one of the above-mentioned items [1] to [18], further containing hyaluronic acid.

[20] A method for producing a sustained drug release sheet, comprising the following steps (1) and (2):
  (1) preparing a solution containing a drug, a biocompatible polymer and a solvent; and
  (2) subjecting the solution to spinning by an electrospinning method to form a non-woven fabric.

[21] A method for producing a sustained drug release sheet, comprising the following steps (1) and (2):
  (1) preparing a solution containing a drug, a biocompatible polymer, a solvent and hyaluronic acid; and
  (2) subjecting the solution to spinning by an electrospinning method to form a non-woven fabric.

[22] A method for producing a sustained drug release sheet, comprising the following steps (1), (2) and (3):
  (1) preparing a solution containing a drug, a biocompatible polymer, a solvent and hyaluronic acid;
  (2) subjecting the solution to spinning by an electrospinning method to form a non-woven fabric; and
  (3) coating the non-woven fabric with hyaluronic acid.

[23] The method for producing a sustained drug release sheet according to any one of the above-mentioned items [20] to [22], wherein the biocompatible polymer is a biodegradable aliphatic polyester or a polyacrylamide derivative.

[24] The production method according to the above-mentioned item [23], wherein the biodegradable aliphatic polyester is selected from the group consisting of polycaprolactone or a copolymer thereof, polylactic acid or a copolymer thereof, polyglycolic acid or a copolymer thereof, and mixtures of these components.

[25] The production method according to the above-mentioned item [23], wherein the polyacrylamide derivative is selected from the group consisting of poly(N-isopropylacrylamide) or a copolymer thereof, poly(2-hydroxyethylmethacrylamide) or a copolymer thereof, a copolymer of N-isopropylacrylamide and 2-hydroxyethylmethacrylamide, and mixtures of these components.

[26] A method for producing a sustained drug release sheet, including the following steps (1) and (2):
  (1) preparing a solution containing a drug, polycaprolactone or a copolymer thereof, and a solvent selected from TFE (2,2,2-trifluoroethanol), HFIP (1,1,1,3,3,3-hexafluoro-2-propanol), chloroform and DMF (N,N-dimethylformamide); and
  (2) subjecting the solution prepared in step (1) to spinning by an electrospinning method under the conditions of a voltage of 10 to 30 kV, a flow rate of 0.1 to 1 m/h and a needle size of 18 to 24 G to form a non-woven fabric on an electrode surface.

[27] The production method according to the above-mentioned item [26], wherein the polycaprolactone or a copolymer thereof has a weight average molecular weight of 1000 to 300000, has 1 to 8 branches per molecule, and contains a DL-lactide in an amount of 0 to 50 mol %.

[28] The production method according to any one of the above-mentioned items [20] to [27], wherein the drug is vitamin B12.

[29] The production method according to any one of the above-mentioned items [20] to [27], wherein the drug is an extract from inflamed skins of rabbits inoculated with vaccinia virus or a fraction thereof.

[30] The production method according to any one of the above-mentioned items [20] to [27], wherein the drug is a neurotrophin.

[31] The production method according the above-mentioned item [30], wherein the neurotrophin is NGF or BDNF.

[32] A method for treating nerve injury, including applying a sustained drug release sheet containing a non-woven fabric that is formed from nanofibers containing a drug having a therapeutic effect on nerve injury and a biocompatible polymer to a patient who need a treatment.

[33] The method according to the above-mentioned item [32], wherein the drug is vitamin B12.

[34] The treatment method according to the above-mentioned item [32], wherein the drug is an extract from inflamed skins of rabbits inoculated with vaccinia virus or a fraction thereof.

[35] The treatment method according to the above-mentioned item [32], wherein the drug is a neurotrophin.

[36] The treatment method according to the above-mentioned item [35], wherein the neurotrophin is NGF or BDNF.

[37] The treatment method according to any one of the above-mentioned items [32] to [36], wherein the biocompatible polymer is a biodegradable aliphatic polyester or a polyacrylamide derivative.

[38] The treatment method according to the above-mentioned item [37], wherein the biodegradable aliphatic polyester is selected from the group consisting of polycaprolactone or a copolymer thereof, polylactic acid or a copolymer thereof, polyglycolic acid or a copolymer thereof, and mixtures of these components.

[39] The treatment method according to the above-mentioned item [37], wherein the polyacrylamide derivative is selected from the group consisting of poly(N-isopropylacrylamide) or a copolymer thereof, poly(2-hydroxyethylmethacrylamide) or a copolymer thereof, a copolymer of N-isopropylacrylamide and 2-hydroxyethylmethacrylamide, and mixtures of these components.

[40] The treatment method according to any one of the above-mentioned items [32] to [39], wherein the Young's modulus of the sheet is 100 kPa to 100 MPa.

[41] The treatment method according to any one of the above-mentioned items [32] to [40], wherein the weight of the sheet is 1 to 100 mg/cm².

[42] The treatment method according to any one of the above-mentioned items [32] to [41], wherein the application is the implantation into the periphery of a nerve injury site.

[43] A use of vitamin B12 for the production of a sustained drug release sheet containing a non-woven fabric that is formed from nanofibers containing a drug having a therapeutic effect on nerve injury and a biocompatible polymer.

[44] A use of an extract from inflamed skins of rabbits inoculated with vaccinia virus or a fraction thereof for the production of a sustained drug release sheet containing a non-woven fabric that is formed from nanofibers containing a drug having a therapeutic effect on nerve injury and a biocompatible polymer.

[45] A use of a neurotrophin for the production of a sustained drug release sheet containing a non-woven fabric that is formed from nanofibers containing a drug having a therapeutic effect on nerve injury and a biocompatible polymer.

[46] The use according to the above-mentioned item [45], wherein the neurotrophin is NGF or BDNF.

[47] The use according to any one of the above-mentioned items [43] to [46], wherein the biocompatible polymer is a biodegradable aliphatic polyester or a polyacrylamide derivative.

[48] The use according to the above-mentioned item [47], wherein the biodegradable aliphatic polyester is selected from the group consisting of polycaprolactone or a copolymer thereof, polylactic acid or a copolymer thereof, polyglycolic acid or a copolymer thereof, and mixtures of these components.

[49] The use of according to the above-mentioned item [47], wherein the polyacrylamide derivative is selected from the group consisting of poly(N-isopropylacrylamide) or a copolymer thereof, poly(2-hydroxyethylmethacrylamide) or a copolymer thereof, a copolymer of N-isopropylacrylamide and 2-hydroxyethylmethacrylamide, and mixtures of these components.

[50] The use according to any one of the above-mentioned items [43] to [49], wherein the Young's modulus of the sheet is 100 kPa to 100 MPa.

[51] The use according to any one of the above-mentioned items [43] to [50], wherein the weight of the sheet is 1 to 100 mg/cm².

Advantages of the Invention

According to the present invention, it becomes possible to provide: a sustained drug release sheet for treating nerve injury, which can be applied by the implantation into the periphery of an injury site so that the concentration of a drug in the site can be kept at a proper level for a long period, thereby enhancing nerve regeneration; a method for producing the sustained drug release sheet; and others.

MODE FOR CARRYING OUT THE INVENTION

Figure 1:
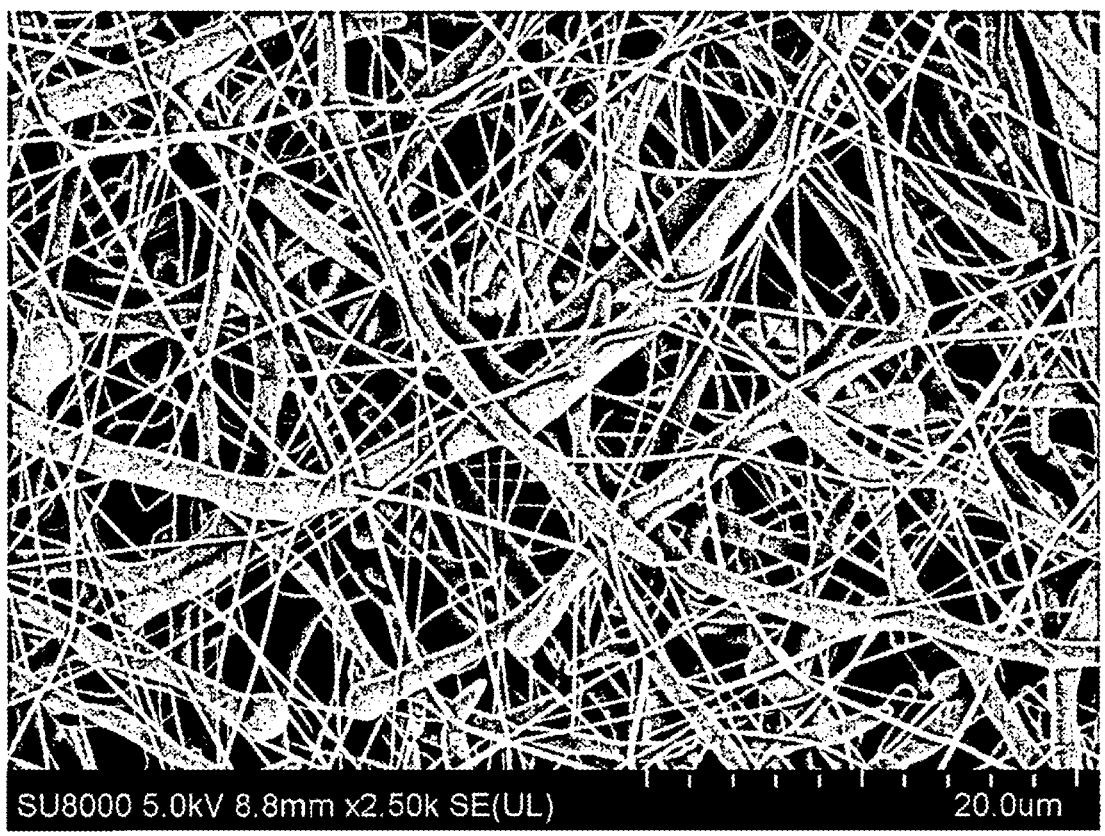
FIG. 1 illustrates the result of the observation of a produced polycaprolactone sheet with a scanning electron microscope (SEM).

The present invention provides a sustained drug release sheet for treating nerve injury. The sustained drug release sheet according to the present invention includes a non-woven fabric that is formed from nanofibers containing a drug such as vitamin B12 and a biocompatible polymer such as a biodegradable aliphatic polyester, and is implanted into the periphery of a nerve injury site upon use. The drug to be contained in the sustained drug release sheet according to the present invention may be any one, as long as the drug has a therapeutic effect on nerve injury. The drug may be selected from vitamin B12, an extract from tissues inoculated with vaccinia virus or a fraction thereof, a neurotrophin such as NGF and BDNF, and others. The drug can treat nerve injury effectively by acting on a nerve injury site to accelerate nerve regeneration. The sustained drug release sheet according to the present invention also includes, within the scope thereof, one containing hyaluronic acid in addition to the above-mentioned drug.

The diseases to which the present sheet is to be applied is nerve injury. Since the sustained drug release sheet according to the present invention has a nerve regeneration enhancement activity, the sustained drug release sheet can treat both of continuity nerve injury and discontinuity nerve injury and is therefore very useful. An example of continuity nerve injury is entrapment neuropathy (a state where nerves are compressed by the surrounding tissues). The sustained drug release sheet according to the present invention is also effective for the enhancement of the regeneration of nerves after neurorrhaphy (a state where nerves are sutured directly after nerve injury), nerves after neurolysis and nerves after nerve grafting (a state where nerve grafting was carried out at a nerve injury site to provide continuity). The sustained drug release sheet according to the present invention can also exhibit an effect to enhance the treatment of discontinuity nerve injury when used alone or in combination with artificial nerve conduits.

Examples of vitamin B12 that is a drug to be contained in the present sheet include cobalamin and derivatives thereof. Specific examples of vitamin B12 include methylcobalamin, cyanocobalamin, hydroxocobalamin, sulphitocobalamin, adenosylcobalamin and salts thereof, and any one of these compounds can be used suitably as an active ingredient for the sustained release agent of the present invention. Among these compounds, methylcobalamin, cyanocobalamin, hydroxocobalamin or a salt thereof is preferred, and methylcobalamin or a salt thereof is more preferred. The content of vitamin B12 is preferably about 1% to about 30%, more preferably about 2% to about 10%, as a final concentration thereof.

The present sheet is composed of a non-woven fabric formed from nanofibers containing a drug and a biocompatible polymer. Each of the nanofibers means a fibrous substance having a diameter of about 10 nm to about 1000 nm and a length that is 100 times or more as large as the diameter. Examples of the biocompatible polymer to be used in the present invention include a biodegradable aliphatic polyester and a polyacrylamide derivative. Preferred examples of the biodegradable aliphatic polyester include polycaprolactone, polylactic acid, polyglycolic acid, polyglycerol acid, polyhydroxyalkanoic acid, poly(butylene succinate), copolymers thereof, and derivatives thereof. From the viewpoint of flexibility and the like, the biodegradable aliphatic polyester is more preferably one selected from the group consisting of polycaprolactone or a copolymer thereof, polylactic acid or a copolymer thereof, polyglycolic acid or a copolymer thereof, and mixtures of these components. Specific examples of the copolymer include a polylactic acid-polycaprolactone copolymer, poly(ε-caprolactone-co-DL-lactide) and the like. Specific examples of the polyacrylamide derivative include poly(N-isopropylacrylamide) or a copolymer thereof, poly(2-hydroxyethylmethacrylamide) or a copolymer thereof, and mixtures of these components. A specific example of the above-mentioned copolymer is poly(N-isopropylacrylamide), and a copolymer of N-isopropylacrylamide and 2-hydroxyethylmethacrylamide.

Each of the nanofibers may contain at least one type of the biocompatible polymer, which may be a copolymer of a biocompatible polymer other than the biocompatible polymer and the biocompatible polymer or may be a copolymer containing multiple types of the biocompatible polymers. In these cases, the type of the copolymerization may be any one of block copolymerization, random copolymerization, alternating copolymerization and graft copolymerization.

The sheet constituting the sustained drug release sheet according to the present invention preferably has a Young's modulus of about 100 kPa to about 100 MPa, more preferably about 1 MPa to about 50 MPa. The Young's modulus can be determined from a stress-strain curve based on measurement values obtained using a commercially available tensile testing machine (e.g., EZ-S500N (manufactured by Shimadzu Corporation)). The weight of the sheet is preferably 1 to 100 mg/cm$^2$, more preferably 1 to 50 mg/cm$^2$. The thickness of the sheet is preferably about 100 μm to about 1 mm, more preferably about 100 μm to about 500 μm. The area of the sheet is not particularly limited, and the sheet may be cut in a size that fits to the size of an affected site upon use. Alternatively, the sheet may be molded in an easy-to-use size. The size to be molded is, for example, preferably 0.1 to 10 cm$^2$, more preferably 1 to 4 cm$^2$.

The present sheet is implanted into the periphery of a nerve injury site upon use. The present sheet is formed so as to have flexibility, and therefore the form of usage of the sheet can be selected appropriately. More specifically, for a nerve injury site of which the periphery is released and on which nerves are exposed, it is preferred to wound the present sheet around the nerve injury site or to place the present sheet so as to cover the nerve injury site. Subsequently, the peripheral tissues are returned to the original state and the skin was sutured. Since the present sheet can be formed flexibly, the present sheet never applies a stimulus that may adversely affect nerves or the peripheral tissues when placed in the nerve injury site. Therefore, the present sheet can be implanted into the periphery of a nerve injury site upon use. Furthermore, it is not needed to remove the present sheet after the treatment of the injury site. It is preferred to subject the present sheet to a sterilization treatment before use. As for the method for the sterilization, a method by which the drug cannot be decomposed and the shape or physical properties of the sheet cannot be deteriorated is selected preferably. For example, sterilization with radioactive ray and sterilization with plasma can be mentioned.

The present sheet can be produced by preparing a solution containing a drug such as vitamin B12 and a biocompatible polymer such as a biodegradable aliphatic polyester, then producing nanofibers using the solution as a raw material by a known spinning method such as an electrospinning method, a self-assembly method and a phase separation method, and then forming a non-woven fabric by a known method. In the preparation of the solution containing a drug such as vitamin B12 and a biocompatible polymer such as a biodegradable aliphatic polyester (i.e., a raw material solution), a proper solvent can be used. The solvent to be used in the raw material solution is removed during the spinning process and does not remain in the non-woven fabric. Examples of the solvent to be used in the raw material solution include TEF, HFIP, chloroform and DMF. Among these solvents, TEF and the like are preferred.

For applying desired flexibility to the non-woven fabric, the biodegradable aliphatic polyester may contain a monomer component for imparting flexibility. Examples of the monomer component include DL-lactide, D-lactide, L-lactide, D-lactic acid and L-lactic acid. The content of the monomer component for imparting flexibility can be adjusted appropriately depending on the type of the biocompatible polymer used, the type of the monomer component for imparting flexibility and the desired flexibility level. Alternatively, the flexibility of the non-woven fabric can be improved by controlling the molecular weight of the biocompatible polymer or by forming a branched structure in the polymer molecule. It is preferred to adjust the molecular weight and the number of branches properly depending on the type of the biocompatible polymer used.

In the case where polycaprolactone or a copolymer thereof is used as the biodegradable aliphatic polyester among the biocompatible polymers and the sheet is produced by an electrospinning method, it is preferred to employ a production method involving the following steps (1) and (2):

(1) preparing a solution containing a drug, polycaprolactone or a copolymer thereof and a solvent selected from TEF, HEIP, chloroform and DMF; and (2) subjecting the solution prepared in step (1) to spinning by an electrospinning method under the conditions of a voltage of 10 to 30 kV, a flow rate of 0.1 to 1 mL/h and a needle size of 18 to 24 G to form a non-woven fabric on an electrode surface.

It is preferred that the polycaprolactone or a copolymer thereof to be used in step (1) has a weight average molecular weight of 1000 to 300000, 1 to 8 branches per molecule and a DL-lactide content of 0 to 50 mol %. The polycaprolactone or a copolymer thereof is more preferably a polycaprolactone copolymer having a weight average molecular weight of 10000 to 100000, 2 to 7 branches per molecule and a DL-lactide content of 20 to 45 mol %, and is still more preferably a polycaprolactone copolymer having a weight average molecular weight of 30000 to 600000, 3 to 6 branches per molecule and a DL-lactide content of 30 to 45 mol %. The solvent to be used is preferably TEF.

In step (2), the solution (raw material solution) prepared in step (1) is subjected to spinning by an electrospinning method to form a non-woven fabric on an electrode surface. The conditions for the electrospinning method are preferably as follows: a voltage of 10 to 30 kV, a flow rate of 0.1 to 1 mL/h and a needle size of 18 to 24 G, and are more preferably as follows: a voltage of 10 to 15 kV, a flow rate of 0.3 to 0.7 mL/h and a needle size of 22 to 24 G.

In the case where the sheet is produced using, for example, poly(N-isopropylacrylamide) or a copolymer thereof or a copolymer of N-isopropylacrylamide and 2-hydroxyethylmethacrylamide as the polyacrylamide derivative among the biocompatible polymers and employing an electrospinning method, it is preferred to employ a production method involving the following steps (1) and (2):

(1) preparing a solution containing a drug, poly(N-isopropylacrylamide) or a copolymer thereof or a copolymer of N-isopropylacrylamide and 2-hydroxyethylmethacrylamide and a solvent selected from TEF, HEIP, chloroform and DMF; and (2) subjecting the solution prepared in step (1) to spinning by an electrospinning method under the conditions of a voltage of 10 to 30 kV, a flow rate of 0.1 to 1 mL/h and a needle size of 18 to 24 G to form a non-woven fabric on an electrode surface.

In step (2), the solution (raw material solution) prepared in step (1) is subjected to spinning by an electrospinning method to form a non-woven fabric on an electrode surface. The conditions for the electrospinning method are preferably as follows: a voltage of 10 to 30 kV, a flow rate of 0.1 to 1 mL/h, and a needle size of 18 to 24 G. The voltage and the flow rate are more preferably 10 to 20 kV and 0.3 to 1 mL/h, respectively.

In addition to the drug such as vitamin B12, the present sheet may further contain hyaluronic acid. Hyaluronic acid may be added to the solution in step (1), or the non-woven fabric formed in step (2) may be soaked in hyaluronic acid to coat the non-woven fabric with hyaluronic acid.

According to the above-mentioned production method, the present sheet for implantation into a living body can be produced, which is composed of nanofibers containing a drug and a biocompatible polymer, and has a Young's modulus of 100 kPa to 100 MPa and a weight of 1 to 100 mg/cm$^2$. The method for producing the present sheet or the use of a drug, nanofiber or a non-woven fabric for the production of the present sheet is also included within the scope of the present invention.

The drug, such as vitamin B12 and a neurotrophin, to be contained in the present sheet may be produced appropriately by a known method or a commercially available product may be purchased. Likewise, hyaluronic acid may also be produced appropriately by a known method or a commercially available product may be purchased.

The present extract to be contained in the present sheet is an extract containing a non-proteinous active substance extracted and separated from the inflamed skin tissues of rabbits by the inoculation of vaccinia virus.

The present extract can be obtained by the following manner: inflamed tissues inflamed by the inoculation with vaccinia virus is crushed; an extraction solvent is added to remove the tissue fragments; then deproteinization is carried out; the deproteinized solution is adsorbed onto an adsorbent; and then the active ingredient is eluted. for example, according to the following process.

(A) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(B) The pH of the extraction liquid is adjusted to be acidic and the liquid is heated for deproteinization. Then, the deproteinized solution is adjusted to be alkaline, heated, and then filtered or centrifuged.

(C) The obtained filtrate or supernatant is made acidic and adsorbed onto an adsorbent such as activated carbon or kaolin.

(D) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits. With regard to a rabbit, any rabbit may be used so far as it belongs to Lagomorpha. Examples thereof include *Oryctolagus cuniculus*, domestic rabbit (domesticated *Oryctolagus cuniculus*), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

Vaccinia virus used herein may be in any strain. Examples thereof include Lister strain, Dairen strain, Ikeda strain, EM-63 strain and New York City Board of Health strain Since the present extract is liquid at the stage of being prepared, it is also possible that said extract is appropriately concentrated or diluted to make into a desired concentration or lyophilized. By fractionating the present extract, it is also possible to obtain the fraction having higher therapeutic effect on nerve injury, which can be used in the present sheet. A more specific method for the manufacture of the present extract is disclosed in, for example, paragraph [0024] to [0027], [0031] and the like in International Publication WO2016/194816.

According to the present invention, it also becomes possible to produce a sustained drug release sheet for treating continuity nerve injury that has been excluded from diseases to which the conventional artificial nerves can be applied. Among peripheral nerve injuries, continuity nerve injury has the incidence of a largest number of patients. Therefore, it is considered that the present invention forms extremely high contribution to continuity nerve injury. In addition, for discontinuity nerve injury, the present sheet can be used alone or in combination with artificial nerves. The present sheet can be implanted into the periphery of a nerve injury site upon use. Therefore, the need to administer a drug at a high dose continuously to increase the concentration of the drug in the blood is eliminated, and the drug can be released sustainably at a local site to accelerate nerve regeneration. Furthermore, the present sheet is formed using a biocompatible polymer and therefore needs not to be removed after a treatment of nerve injury. The present sheet can be formed very flexibly. Therefore, the present sheet does not apply a stimulus that may adversely affect nerves when implanted into the periphery of a nerve injury site, and is therefore very easy to use. When artificial nerves are used, it is generally needed to use a surgery microscope. In contrast, when the present sheet is used singly, it is not needed to use a surgery microscope and the operation is very easy, which are advantageous. That is, the present sheet is very useful, because the present sheet has both of effectiveness and safety and is highly convenient.

EXAMPLES

Hereinbelow, the present invention will be described in detail by reference to the following examples. However, it is not intended that the present invention is limited to these examples.

Example 1: Production of Vitamin B12-Containing Sheet and the Like (1) Production of Polycaprolactone Sheet and the Like To 900 mg of polycaprolactone was added 4.5 mL of HEIP. The resultant solution was subjected to an ultrasonic wave treatment for 3 hours to prepare a liquid dispersion (the concentration of the polymer solution: 20 wt %).

Subsequently, a voltage of 20 kV was applied to the liquid dispersion while feeding the whole of the liquid dispersion at a rate of 1.0 mL/h using a 5-mL syringe. Fibers spun on a metal substrate having an aluminum foil placed thereon were trapped by lamination to produce a polycaprolactone sheet (the syringe needle used: 22 G, the syringe-metal substrate distance: 13 cm).

As shown in the scanning electron microscope (SEM) observation image of FIG. 1, a polycaprolactone sheet composed of a non-woven fabric formed from nanofibers was produced.

Figure 2:
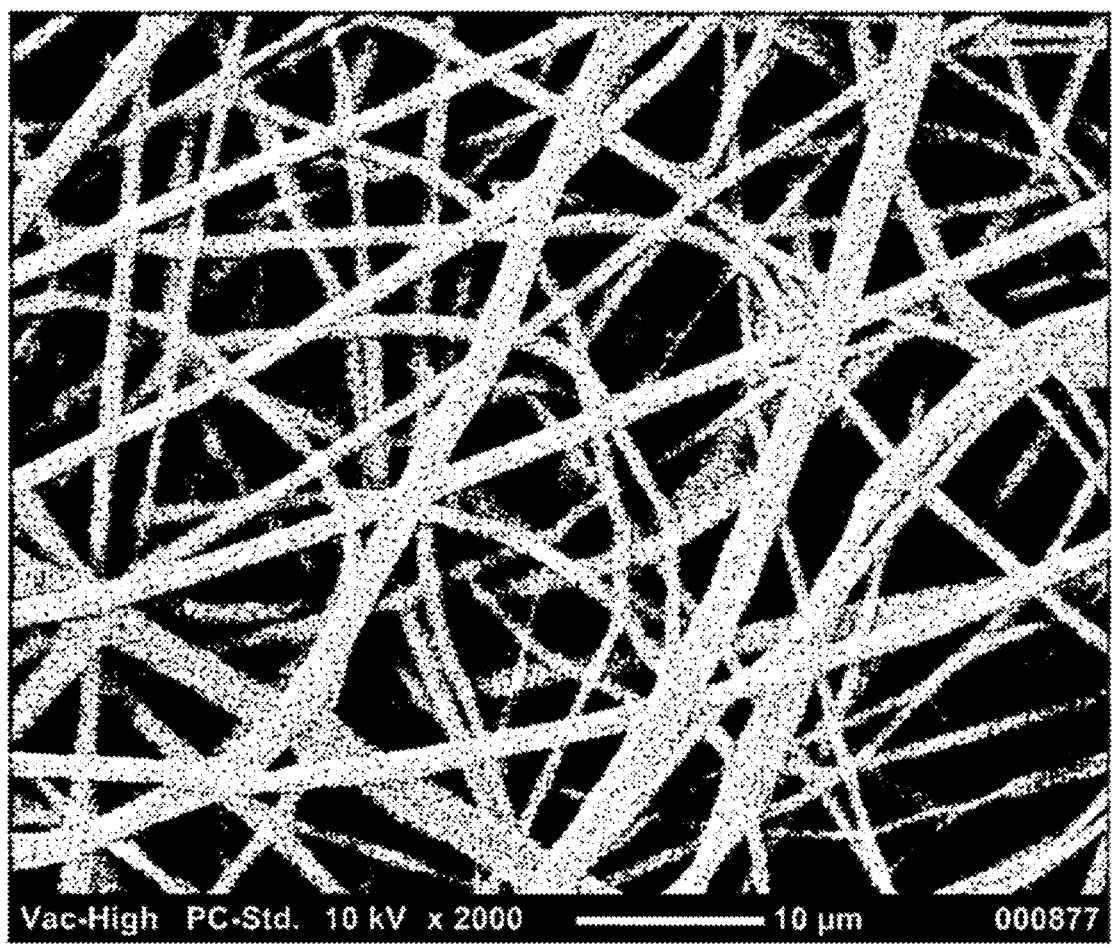
FIG. 2 illustrates the result of the observation of a produced poly(N-isopropylacrylamide) sheet with a SEM.
Figure 3:
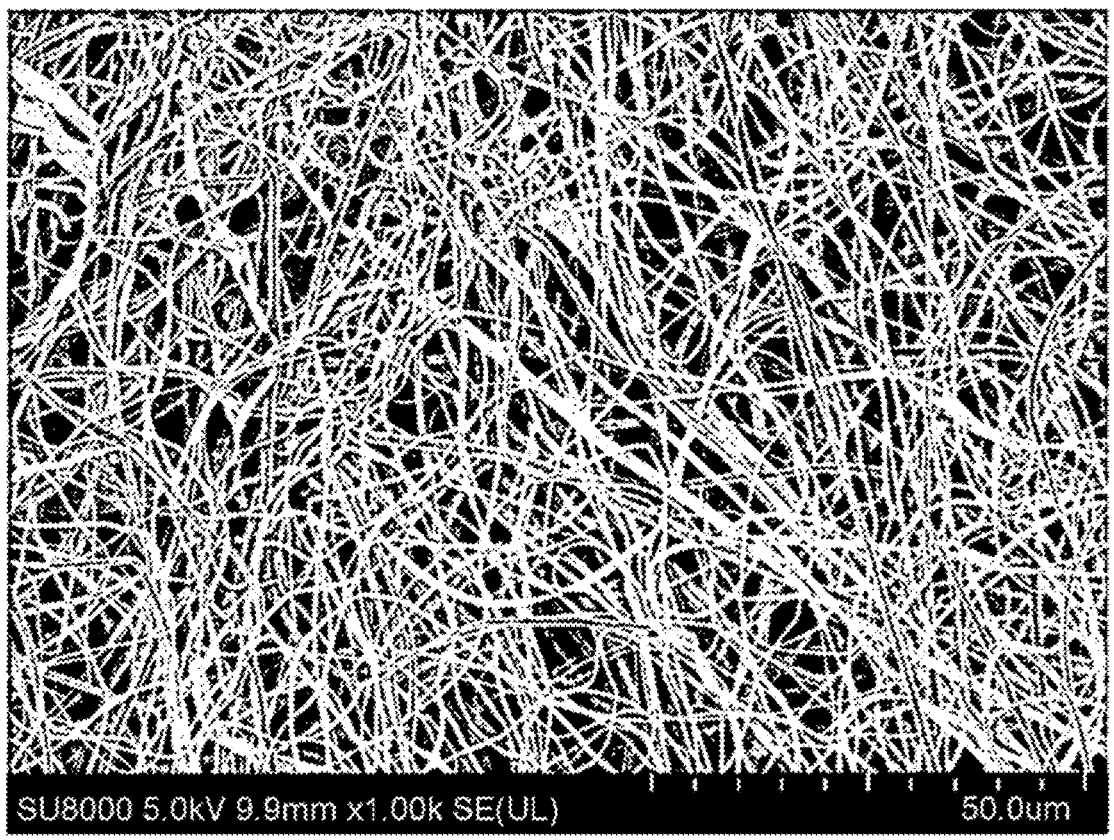
FIG. 3 illustrates the result of the observation of a produced poly(NIPAAm-co-HMAAm) sheet with a SEM.

In the same manner, a fiber sheet using a copolymer of poly(N-isopropylacrylamide), N-isopropylacrylamide and 2-hydroxyethylmethacrylamide (also referred to as "poly (NIPAAm-co-HMAAm)", hereinbelow) was also produced (see FIGS. 2 and 3).

(2) Production of Polycaprolactone Sheet Containing Magnetic Nanoparticles

To 270 mg of magnetic nanoparticles composed of 900 mg of polycaprolactone and $\gamma$-$Fe_2O_3$ was added 4.5 mL of HEIP. The resultant solution was subjected to an ultrasonic wave treatment for 12 hours to prepare a liquid dispersion (the concentration of the polymer solution: 20 wt %).

Figure 4:
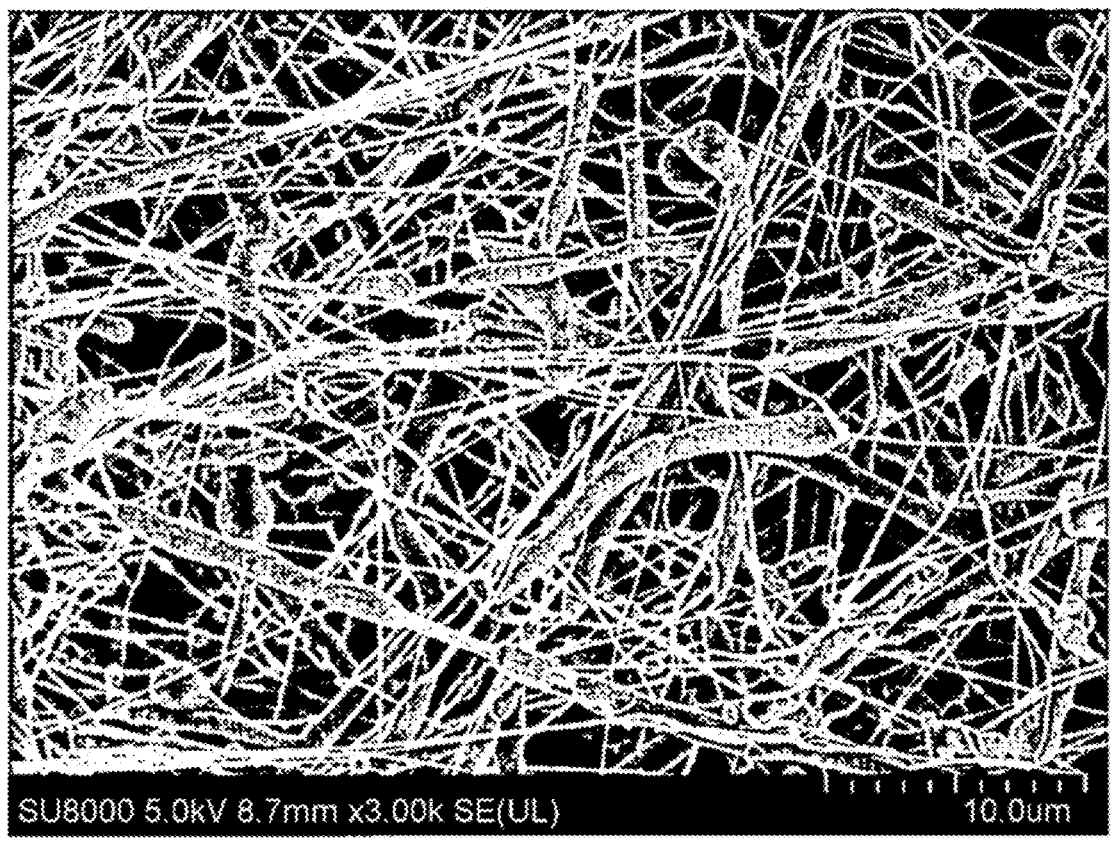
FIG. 4 illustrates the result of the observation of a produced polycaprolactone sheet containing magnetic nanoparticles with a SEM.

Subsequently, a voltage of 20 kV was applied to the liquid dispersion while feeding the whole of the liquid dispersion at a rate of 1.0 mL/h using a 5-mL syringe. Fibers spun on a metal substrate having an aluminum foil placed thereon were trapped by lamination to produce a poly(NIPAAm-co-HMAAm) sheet containing magnetic nanoparticles (the syringe needle used: 22 G, the content of magnetic nanoparticles in the sheet: 30%). As shown in the scanning electron microscope (SEM) observation image of FIG. 4, a magnetic particle-containing polycaprolactone sheet composed of a non-woven fabric formed from nanofibers was produced.

(3) Production of Hyaluronic-Acid-Coated Polycaprolactone Sheet

Figure 5:
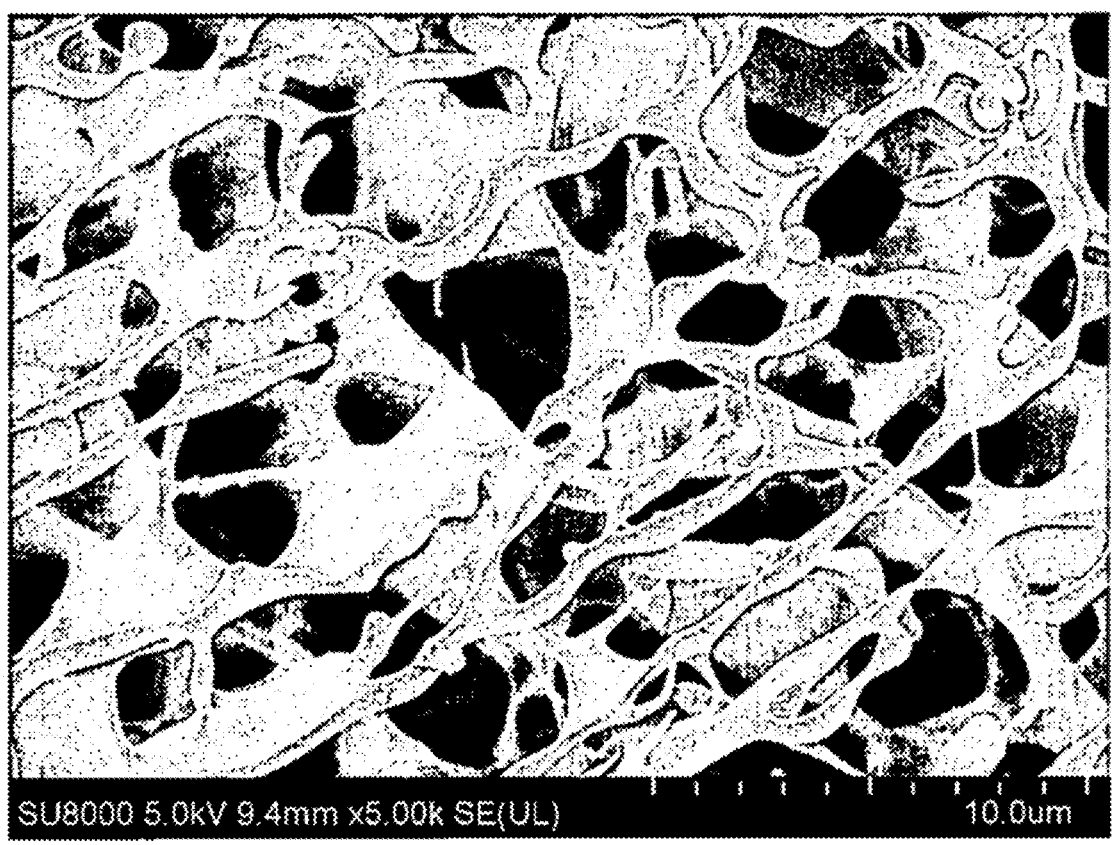
FIG. 5 illustrates the result of the observation of a produced hyaluronic-acid-coated polycaprolactone sheet with a SEM.

Hyaluronic acid in an amount of 128 mg was dissolved in 2.5 mL of pure water to prepare a 5-wt % hyaluronic acid solution. The polycaprolactone sheet produced in Example 1(1) was soaked in the hyaluronic acid solution and was allowed to leave for 24 hours. The resultant product was lyophilized for 72 hours to produce a hyaluronic-acid-coated polycaprolactone sheet. A scanning electron microscope (SEM) observation image of the hyaluronic acid-coated polycaprolactone sheet was shown in FIG. 5.

(4) Production of Vitamin B12-Containing Sheet

In 6 mL of TEF were dissolved 600 mg of poly($\varepsilon$-caprolactone-co-DL-lactide) and methylcobalamin (Sigma). As the poly($\varepsilon$-caprolactone-co-DL-lactide), one having a weight average molecular weight of 40000, 4 branches per molecule and an $\varepsilon$-caprolactone/DL-lactide molar ratio of 60:40 produced by ourselves was used. Methylcobalamin was dissolved in amounts of 6.5 mg, 13 mg and 20 mg to prepare three kinds of solutions so that the final concentrations of the solutions became 1%, 2% and 3%, respectively. Subsequently, nanofibers were produced by employing an electrospinning method, and the nanofibers were formed into a net-like form to produce a non-woven fabric. More specifically, the solution was extruded through a 24-G needle at a flow rate of 0.5 mL/h while applying a voltage of 12 kV to spin the solution, and then the nanofibers were trapped by accumulating on an electrode surface to produce a non-woven fabric.

Figure 7:
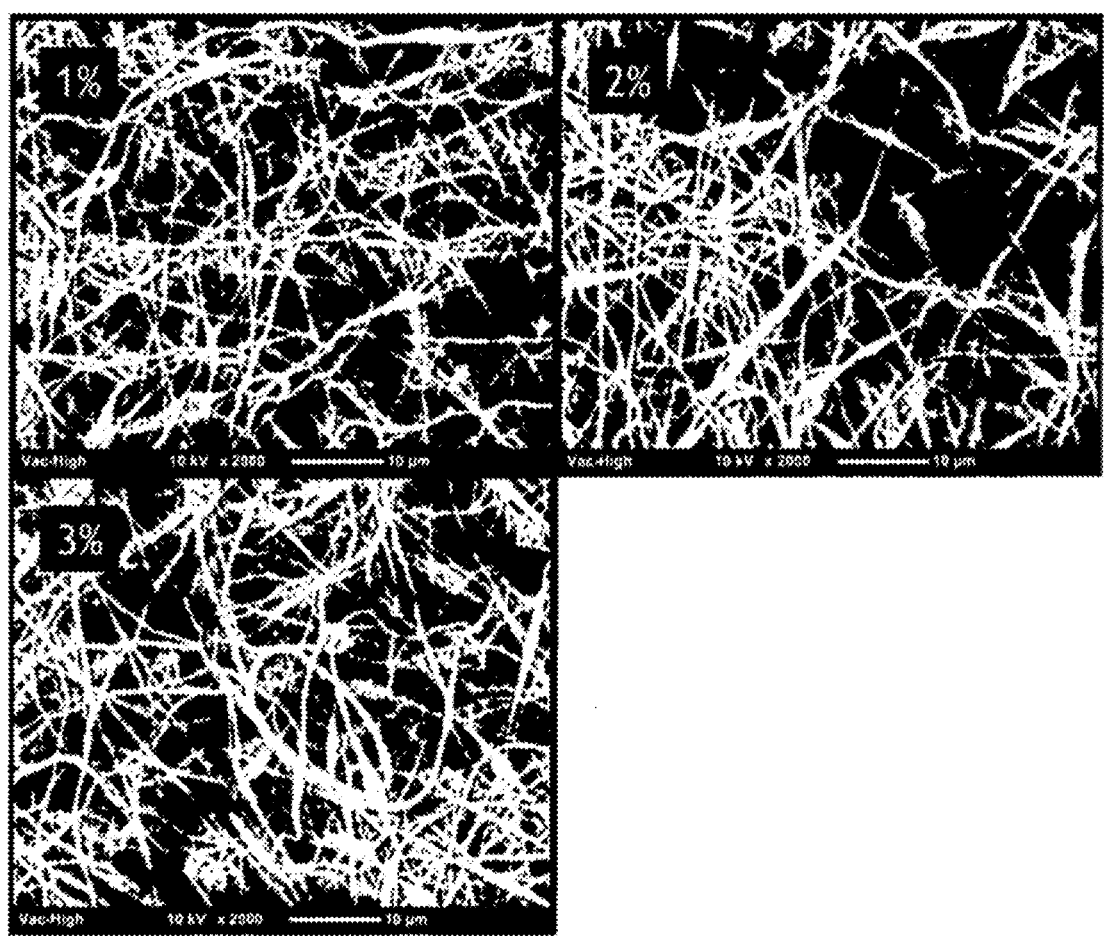
FIG. 7 illustrates the results of the observation of produced three types of the present sheets each containing vitamin B12 with a SEM.

As shown in the scanning electron microscope (SEM) observation image of FIG. 7, a vitamin B12-containing sheet composed of a non-woven fabric formed from nanofibers was produced. The sheet had a thickness of about 300 μm and a weight of about 10 mg/cm$^2$.

In the same manner as mentioned above, sheets respectively containing NGF and BDNF as drugs were produced.

(5) Production of Sheet Containing the Present Extract

To 900 mg of polycaprolactone and 270 mg of the present extract lyophilization powder was added 4.5 mL of HEIP. The resultant solution was subjected to an ultrasonic wave treatment for 3 hours to prepare a liquid dispersion (the concentration of the polymer solution: 20 wt %).

Subsequently, a voltage of 20 kV was applied to the liquid dispersion while feeding the whole of the liquid dispersion at a rate of 0.5 mL/h using a 5-mL syringe. Fibers spun on a metal substrate having an aluminum foil placed thereon were trapped by lamination to produce a sheet containing the present extract (the syringe needle used: 18 G, the amount of the present extract carried on the sheet: 30%).

Figure 6:
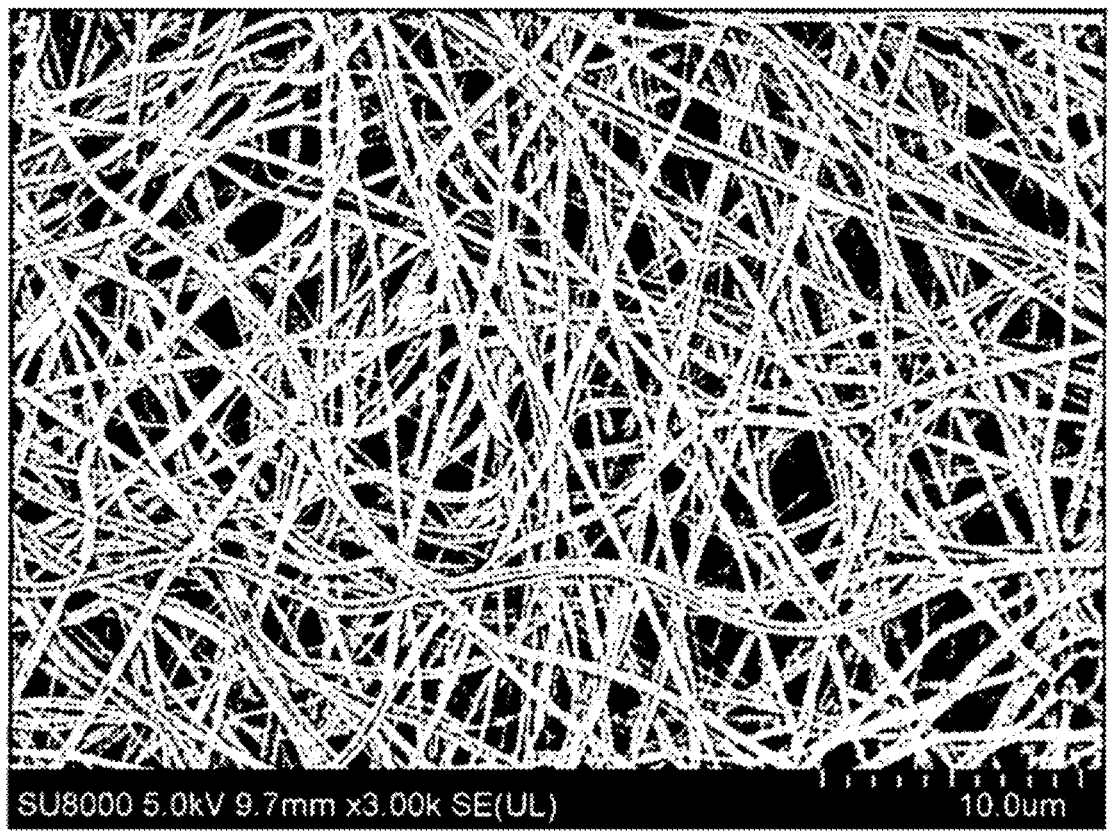
FIG. 6 illustrates the result of the observation of a produced polycaprolactone sheet containing the present extract with a SEM.

A scanning electron microscope (SEM) observation image of the polycaprolactone sheet containing the present extract thus produced is shown in FIG. 6.

Example 2: Confirmation of Sustained Releasability of Vitamin B12-Containing Sheet and Others PBS in a volume of 3 mL was placed in a tube, 10 mg of a sheet was soaked therein, the temperature of the solution was kept at 37° C., the solution was sampled over time, and then the concentration of vitamin B12 was measured. The amount of one sample was 100 μL, and the measurement of a vitamin B12 concentration was carried out by an ultraviolet visible absorbance measurement method.

Figure 8:
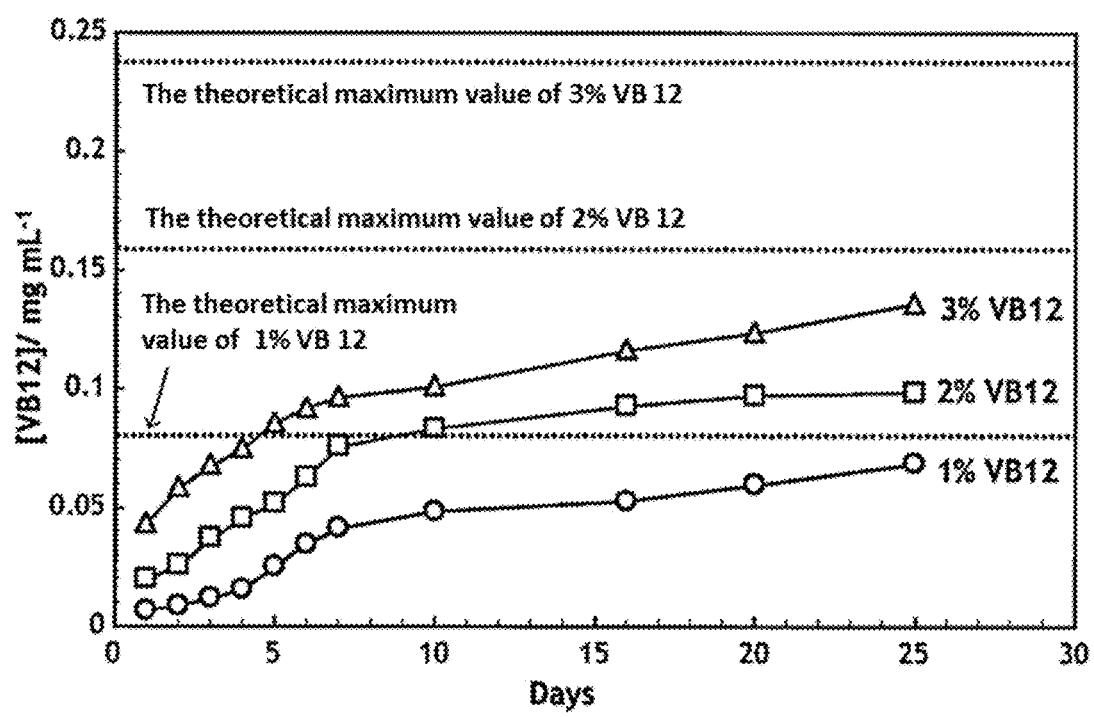
FIG. 8 illustrates the results of the confirmation of the sustained release properties of the produced three types of the present sheets each containing vitamin B12.

The results are shown in FIG. 8. All of the three kinds of sheets showed sustained releasability thereof until day 25. With taking the theoretical maximum value into consideration, it is considered that the sustained released period becomes longer with the increase in the content of methylcobalamin. Although not shown in the drawing, it was confirmed that the three kinds of sheets further showed sustained release for additional 8 weeks (until day 56) thereafter.

In the same manner as mentioned above, the drug sustained releasability of the sheets respectively containing the present extract, NGF and BDNF were also confirmed.

Example 3: Evaluation of Drug Efficacy Using Rat Sciatic Nerve Crush Injury Model 1. Production of Rat Sciatic Nerve Crush Injury Model All of animal experiments were went ahead with the approval of the Ethics Committee of the animal laboratory of Osaka University. Six-week-old male Wistar rats (body weights: about 200 g) were used. All of the surgeries were carried out while applying deep sedation with a mixed anesthetic drug composed of midazolam (2 mg/kg), butorphanol (2.5 mg/kg) and medetomidine (0.15 mg/kg). A left sciatic nerve was exposed under clean operations, and a crush injury was applied to a position 5 mm distal to a sciatic notch with a pair of forceps. The time of crushing was 10 seconds, the frequency of crushing operations was three times, and the intervals between the crushing operations was 10 seconds. The fascia and the skin were sutured together with 4-0 nylon. The experimental rats were divided into the following five groups: a sham group in which only the exposure of the sciatic nerve was carried out without applying crush injury to the sciatic nerve; a CTR sheet group in which only the exposure of the sciatic nerve was carried out without applying crush injury to the sciatic nerve and a sheet that did not contain methylcobalamin was implanted; an untreated group in which crush injury was applied but no treatment was carried out; a MeCbl sheet group in which crush injury was applied and a methylcobalamin-containing sheet (the 3% methylcobalamin-containing sheet produced in Example 1) was implanted; and a MeCbl pump group in which crush injury was applied and methylcobalamin was systemically administered (1 mg/kg/day). The systemic administration of methylcobalamin was performed by placing an osmotic minipump (Model 2ML2; Alzet, Cuperitino, Calif., USA) under the skin of the back. All of the surgeries were carried out by the same practitioner.

The examination on the sheet that contained the present extract as a drug was carried out in the same manner. The experimental rats were divided into the following four groups: a sham group in which only the exposure of the sciatic nerve was carried out without applying crush injury to the sciatic nerve; a CTR sheet group in which only the exposure of the sciatic nerve was carried out without applying crush injury to the sciatic nerve and a sheet that did not contain the present extract was implanted; an untreated group in which crush injury was applied but no treatment was carried out; and a NTP sheet group in which crush injury was applied and a sheet containing the present extract (the sheet containing the present extract which was produced in Example 1) was implanted.

Each of the sheets respectively contained NGF and BDNF as drugs was also able to be implanted into a model rat in which a sciatic nerve was crush-injured.

2. Evaluation Items and Experiment Method
(1) Concentration of Vitamin B12 in Blood Blood was collected in an amount of 1 mL from the left ventricle of a rat under anesthesia 6 weeks after the surgery. The collected blood was centrifuged at 800×g for 20 minutes to collect a supernatant. The measurement of a concentration of vitamin B12 in the blood was entrusted to BML, INC. (Tokyo).

(2) Evaluation of Motor and Sensory Functions

For the evaluation of a motor function, a sciatic function index (SFI) was measured 6 weeks after the surgery. For the measurement of an SFI, an ink was applied to the back paw of a rat, then the rat was allowed to walk on office paper placed on a 40 cm-square horizontal table, and then foot prints of the rat were recorded. The four items mentioned below were measured to calculate an SFI. The rating "SFI=0" means that the function was normal, and the rating "SFI=−100" means that the function was impaired. In the evaluation, an individual which underwent necrosis in the toe or the loss of the toe was excluded. An SFI value was calculated in accordance with the following mathematical formula. The items are as follows.

SFI=−38*((EPL−NPL)/NPL+109.5*((ETS−NTS)/NTS)+13.3*((EITS−NITS)−8
EPL: experimental print length
NPL: normal print length
ETS: experimental toe spread
NTS: normal toe spread
EIT: experimental intermediary toe spread
NIT: normal intermediary toe spread For the evaluation of a sensory function, a mechanical hind paw withdrawal threshold was measured 6 weeks after the surgery using a von Frey filament (0.008 to 26 g; Touch Test, North Coast Medical Inc, Gilroy, Calif., USA). Each of the rats was made walk on a metallic mesh, then a pressure was applied onto the center of the sole until the filament began to bend, and then a value at which the rat evoked an escape behavior was recorded.

(3) Electrophysiological Evaluation

Each of the rats 3 or 6 weeks after the surgery was sedated with an anesthetic drug and was then placed on an operating table in a prone position. A left sciatic nerve and a left tibialis anterior muscle were exposed. Each of a compound muscle action potential (CMAP) and a terminal latency (TL) was measured while stimulating a proximal site of a sciatic nerve with a bipolar electrode. A nerve conduction velocity (NCV) was calculated from measurement values respectively obtained at a proximal site and a distal site to the sciatic nerve crush injury while stimulating the positions with a bipolar electrode. In the measurement and the evaluation, AD Instruments Power Lab 2/26, Stimulus isolater, and Bio Amp and Chart & Scope software (all manufactured by AD Instruments, Bel la Vista, NSW, Australis) were used.

(4) Histological Evaluation

Each of the rats 6 weeks after the surgery was sedated with an anesthetic drug, and a left sciatic nerve was collected therefrom and then fixed with 4% PFA for 5 days and with 20% sucrose for 24 hours and then frozen and embedded. An embedded tissue was sliced at a thickness of 5 μm in a neural short axis direction, and was placed on a glass slide. The sliced tissue was dried for 1 hour, and was then fixed with 95% methanol for 30 minutes. After blocking, a primary antibody was allowed to react at 4° C. overnight. A secondary antibody was allowed to react at room temperature for 1 hour to label the nucleus with DAPI. As the primary antibody, each of an anti-neurofilament 200 (NF200) antibody produced in rabbit (1:1000; 102M4784, SIGMA), which was an indicator for an axon, and Anti-Myelin Basic Protein (MBP) Mouse mAb (1:1000; NE1018, CALIOCHEM), which was an indicator for a myelin sheath, was used. As the secondary antibody, each of Alexa 488 labeled goat anti-rabbit IgG antibody (1:1000; Lifetechnologies) and Alexa 568 labeled goat anti-mouse IgG antibody (1:1000; Lifetechnologies) was used. The total number of axons and the ratio of myelinated axons (total number of MBP-positive axons)/(total number of axons) were evaluated.

Example 4: Evaluation of Drug Efficacy Using Rat Sciatic Nerve-Deficient Model

1. Production of Rat Sciatic Nerve-Deficient Model

Six-week-old male Wistar rats (body weight: about 200 g) were used. All of the surgeries were carried out while applying deep sedation with a mixed anesthetic drug composed of midazolam (2 mg/kg), butorphanol (2.5 mg/kg) and medetomidine (0.15 mg/kg). A left sciatic nerve was exposed under clean operations, and a sciatic nerve was cut at a position 5 mm distal to a sciatic notch and a position further 10 mm distal to the aforementioned position to produce a 10 mm deficient model.

The experimental rats were divided into the following four groups: (i) an artificial nerve conduit+MeCbl sheet group; in which cut ends of a sciatic nerve were sutured to the respective both ends of an artificial nerve conduit having a diameter of 1.5 mm and a length of 12 mm with 10-0 nylon in such a manner that each of the cut ends was drawn by 1 mm into each of the both ends, and then a methylcobalamin-containing sheet having a width of 10 mm and a length of 14 mm was placed so as to cover the sutured parts; (ii) an artificial nerve conduit group; in which cut ends of a sciatic nerve were sutured to the respective both ends of an artificial nerve conduit with 10-0 nylon in such a manner that each of the cut ends was drawn by 1 mm into each of the both ends; (iii) an autologous transplant graft group; in which a cut sciatic nerve was inversed and was then sutured with 10-0 nylon; and (iv) a sham group: only the exposure of a sciatic nerve was carried out. The fascia was sutured to the skin with 4-0 nylon. All of the surgeries were carried out by the same practitioner.

Likewise, a sheet containing the present extract, NGF or BDNF as a drug was also able to be implanted into a sciatic nerve-deficient model rat.

2. Evaluation Items and Experimental Methods (1) Evaluation of Sensory Function

For the evaluation of a sensory function, a mechanical hind paw withdrawal threshold was measured 12 weeks after the surgery in the same manner as in Example 3-2 (2).

(2) Electrophysiological Evaluation

A TL and an NCV were calculated 12 weeks after the surgery in the same manner as in Example 3-2 (3).

(3) Histological Evaluation

Each of the rats 12 weeks after the surgery was sedated with an anesthetic drug, and a left sciatic nerve was collected therefrom and then fixed with 4% PFA for 7 days and with 20% sucrose for 24 hours and then frozen and embedded. The total number of axons and the ratio of myelinated axons (total number of MBP-positive axons)/(total number of axons) were evaluated in the same manner as in Example 3-2 (4).

(4) Statistical Processing

All of the numerical values were expressed in mean±SEM. In Examples 3-2 (1) to (4) and Example 4, the statistical processing was performed by a Tukey-Kramer HSD test using JMP software version 11 (SAS Institute).

In Test Example 3-2 (5), the statistical analysis was performed using SAS System Version 9.1.3 (SAS Institute), and the two-group comparison was performed by a F test, wherein a Student's t test was performed when the dispersion was homoscedastic and a Welch's test was performed when the dispersion was heteroscedastic.

3. Results

Figure 9:
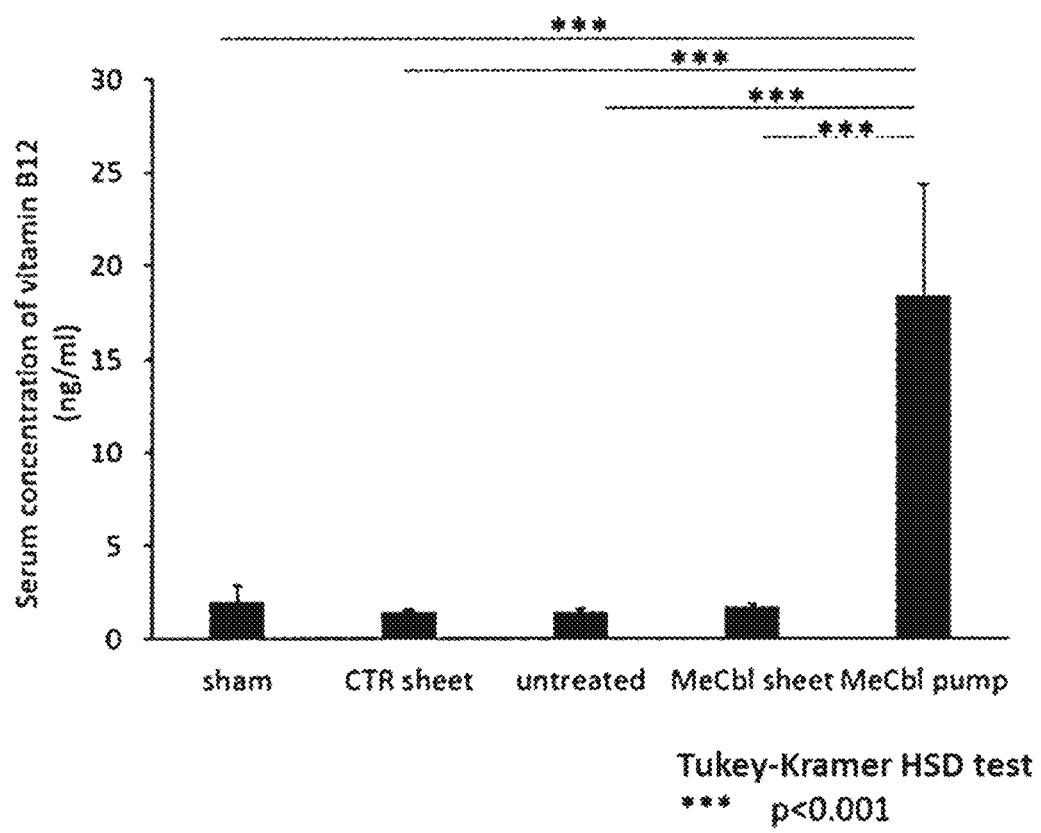
FIG. 9 illustrates the results of an experiment for evaluating the drug efficacy of the present sheet containing vitamin B12 using a rat sciatic nerve crush injury model, wherein the concentration of vitamin B12 in the blood was measured during the 6th week after a surgery.

A. Evaluation of Drug Efficacy Using Rat Sciatic Nerve Crush Injury Model (1) Concentration of Vitamin B12 or the Like in Blood The results are shown in FIG. 9. In the MeCbl pump group (18.35±2.27 ng/mL), a significant increase in the concentration in the blood was observed. However, in the MeCbl sheet group (1.73±0.05 ng/mL), the increase in the concentration in the blood was not observed. In all of the drug-unadministered groups (the sham group: 1.99±0.33 ng/mL, the CTR sheet group: 1.48±0.05 ng/mL and the untreated group: 1.50±0.07 ng/mL), the increase in the concentration in the blood was not observed.

When the present extract, NGF or BDNF was used as a drug, the increase in the concentration in the blood was not observed, either.

(2) Evaluation of Motor Function and Sensory Function

Figure 10:
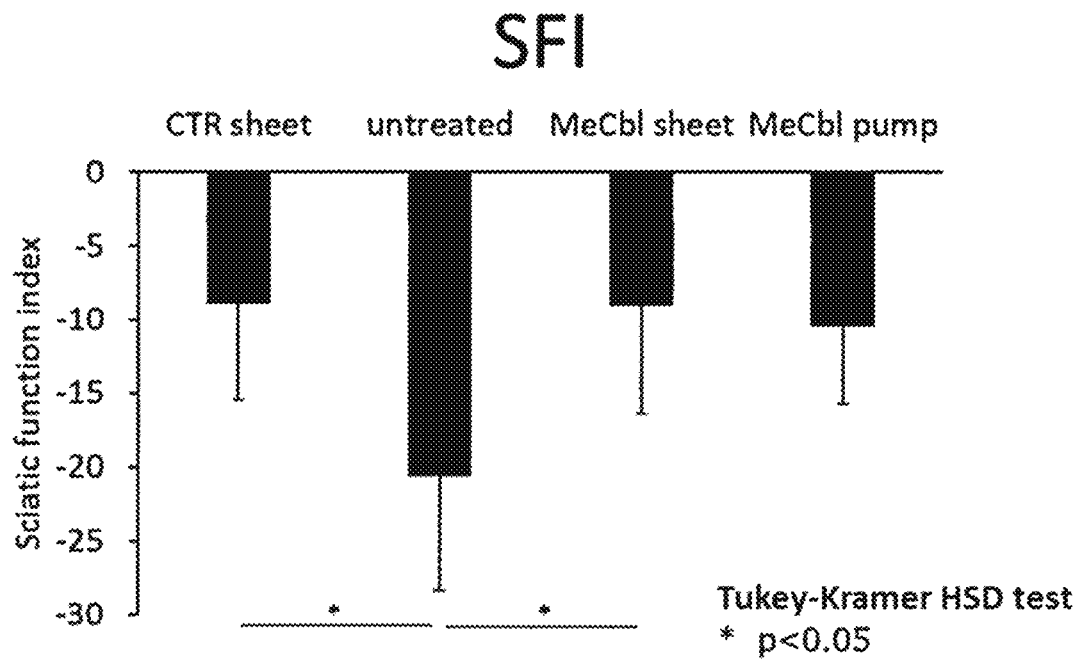
FIG. 10 illustrates the results of an experiment for evaluating the drug efficacy of the present sheet containing vitamin B12 using a rat sciatic nerve crush injury model, wherein a sciatic function index (SFI) was measured during the 6th week after a surgery to evaluate a motor function.

The results of the SFIs are shown in FIG. 10. Compared with the untreated group (−20.6±4.2), significant improvement was observed in the MeCbl sheet group (−9.0±2.0) and a recovery tendency was observed in the MeCbl pump group (−10.5±2.0).

Figure 11:
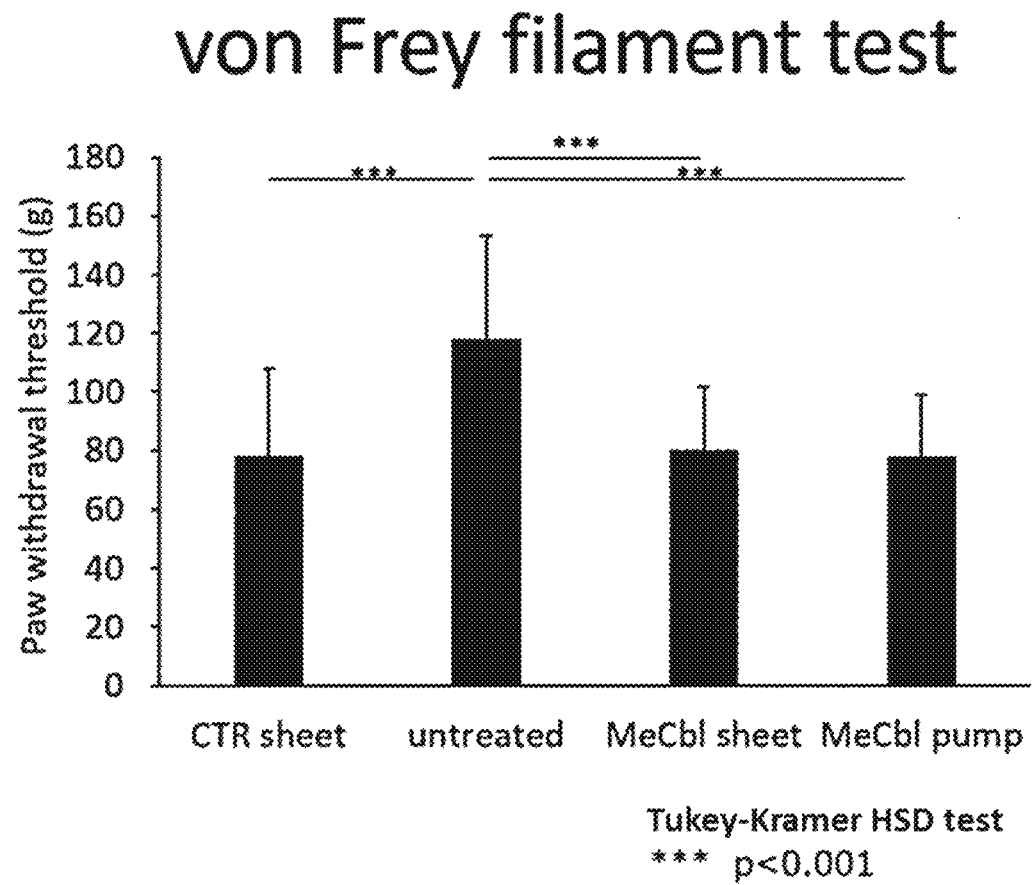
FIG. 11 illustrates the results of an experiment for evaluating the drug efficacy of the present sheet containing vitamin B12 using a rat sciatic nerve crush injury model, wherein a von Frey filament test was carried out during the 6th week after a surgery to evaluate a sensory function.

The results of the von Frey filament test are shown in FIG. 11. Compared with the untreated group (117.8±11.7 g), significant improvement was observed in the MeCbl sheet group (80±7.6 g) like the MeCbl pump group (77.8±7.0 g).

Figure 12:
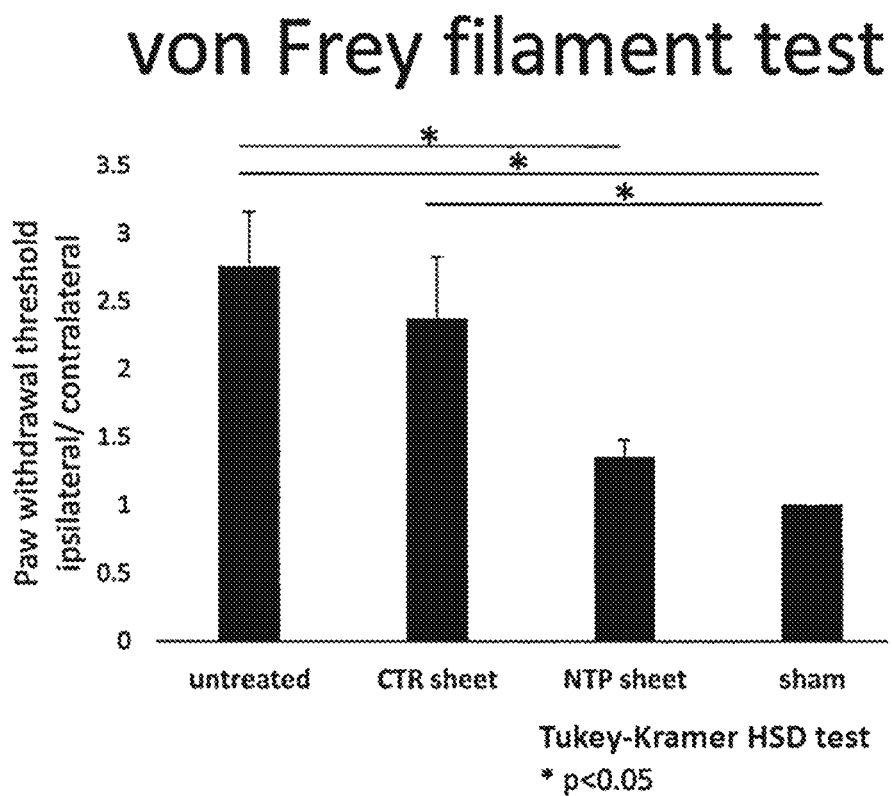
FIG. 12 illustrates the results of an experiment for evaluating the drug efficacy of the present sheet containing the present extract using a rat sciatic nerve crush injury model, wherein a von Frey filament test was carried out during the 3rd week after a surgery to evaluate a sensory function.

The results of the von Frey filament test for the sheet containing the present extract as a drug are shown in FIG. 12. Compared with the untreated group (2.75±0.41), significant improvement was observed in the NTP sheet group (1.35±0.13).

When the sheet containing, as a drug, NGF or BDNF was implanted, the improvement in the motor function and the sensory function was also observed.

(3) Electrophysiological Evaluation

Figure 13:
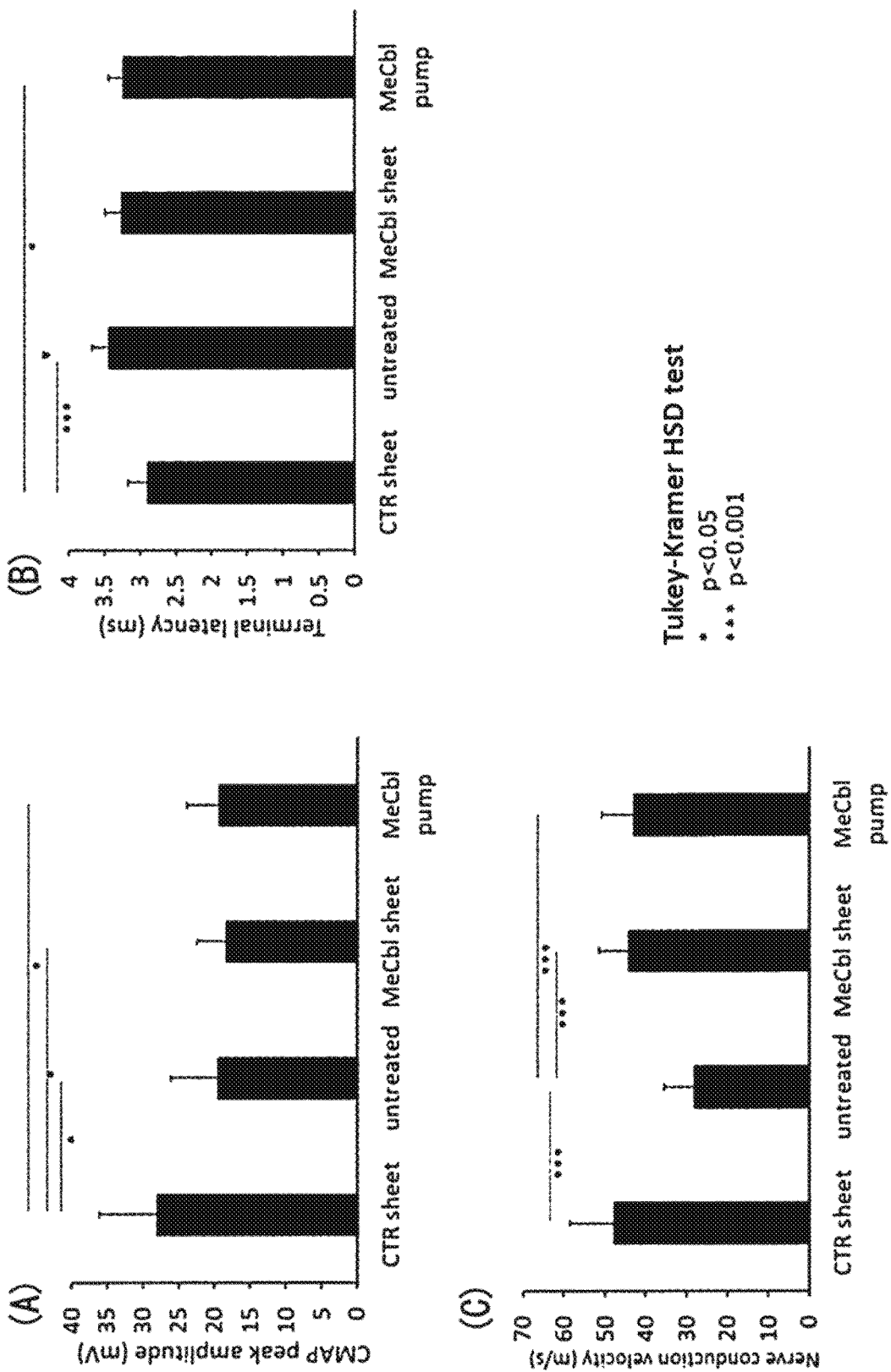
FIG. 13 illustrates the results of an experiment for evaluating the drug efficacy of the present sheet containing vitamin B12 using a rat sciatic nerve crush injury model, wherein an electrophysiological evaluation was carried out during the 6th week after a surgery, and panel (A) illustrates the results of a compound muscle action potential (CMAP), panel (B) illustrates the results of a terminal latency (TL), and panel (C) illustrates the results of a nerve conduction velocity (NCV).

The results are shown in FIG. 13. Panel (A) shows the results of the CMAPs, the panel (B) shows the results of the TLs, and the panel (C) shows the results of the NCVs. In the CMAPs and TLs, compared with the untreated group (CMAP: 19.5±2.3 mV, TL: 3.45±0.08 ms), significant improvement was not observed in the MeCbl sheet group (CMAP: 18.5±1.5 mV, TL: 3.27±0.09 ms) and the MeCbl pump group (CMAP: 19.5±1.5 mV, TL: 3.24±0.07 ms). In contrast, with respect to NCVs, compared with the untreated group (28.2±2.5 m/s), significant improvement was observed in both of the MeCbl sheet group (44.4±2.8 m/s) like the MeCbl pump group (43.2±2.5 m/s).

When the sheet containing, as a drug, the present extract, NGF or BDNF was implanted, the improvement was also observed.

(4) Histological Evaluation

Figure 14:
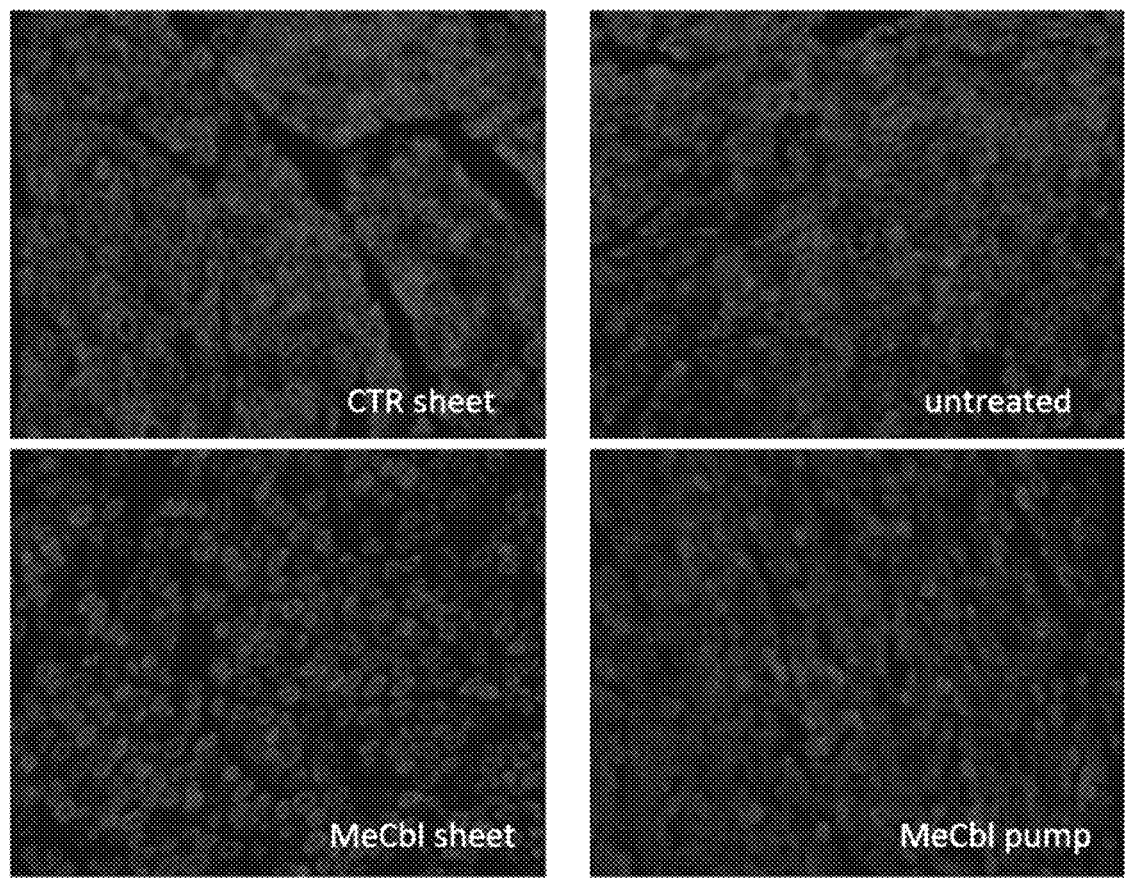
FIG. 14 illustrates the results of an experiment for evaluating the drug efficacy of the present sheet containing vitamin B12 using a rat sciatic nerve crush injury model, wherein a sciatic nerve was collected during the 6th week after a surgery and was then immunostained with an anti-Myelin Basic Protein (MBP) antibody that is an indicator for a myelin sheath.
Figure 15:
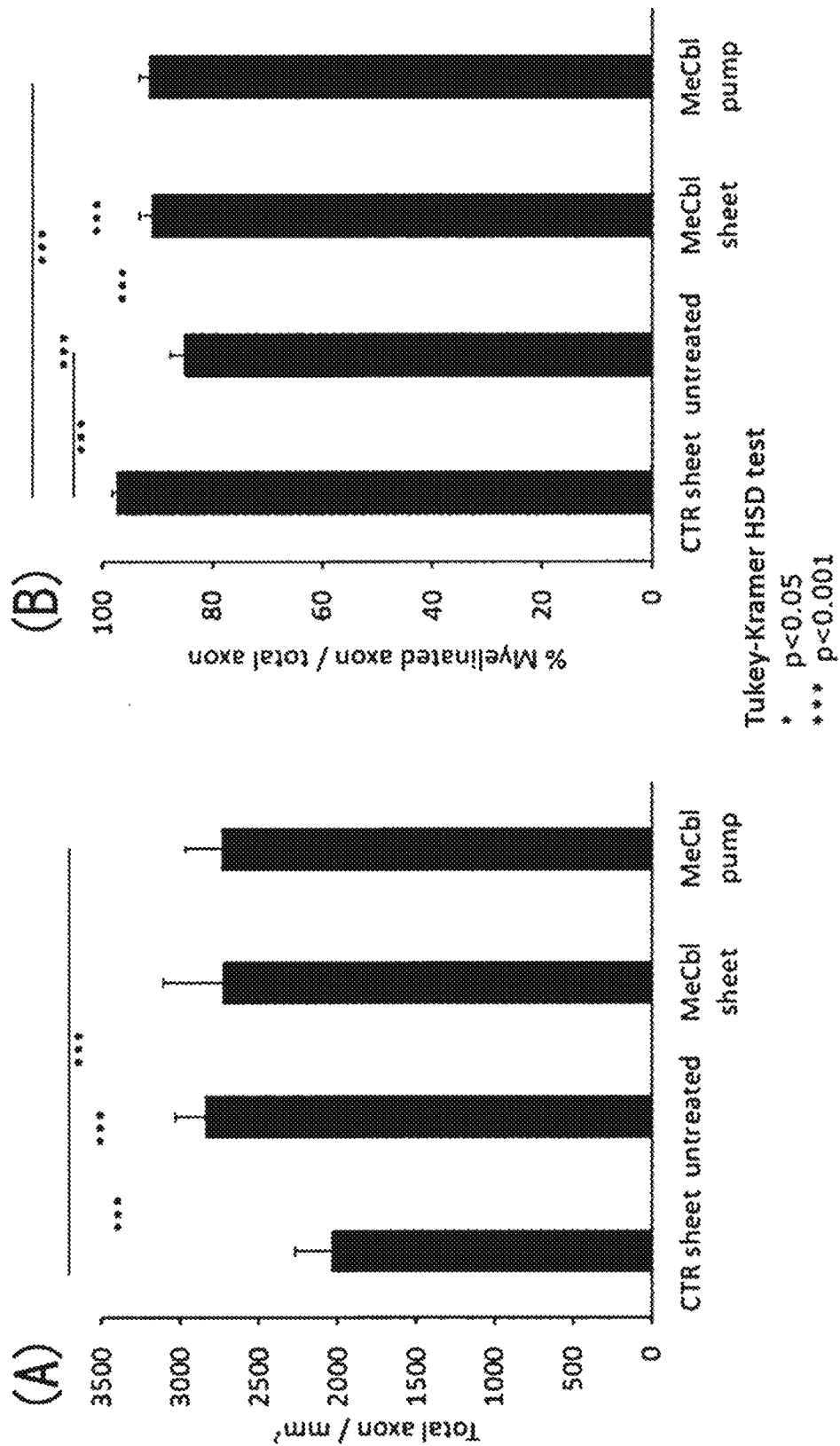
FIG. 15 illustrates the results of an experiment for evaluating the drug efficacy of the present sheet containing vitamin B12 using a rat sciatic nerve crush injury model, wherein a histological evaluation was carried out during the 6th week after a surgery, and panel (A) shows the results of the total number of axons and panel (B) shows the results of the (number of MBP-positive axons)/(total number of axons).

The results are shown in FIGS. 14 and 15. In FIG. 14, microscopic images obtained by immunostaining myelin sheaths with an anti-MBP antibody are shown, wherein whitish parts are stained myelin sheaths. FIG. 15(A) shows the results of the total number of axons, and FIG. 15(B) shows the results of the ratio of myelinated axons (number of MBP-positive axons)/(total number of axons).

With respect to the number of regenerated axons per sq. mm, a significant difference was not observed among the untreated group (2843±68/mm$^2$), the MeCbl sheet group (2733±142/mm$^2$) and the MeCbl pump group (2735±77/mm$^2$). With respect to the ratio of myelinated axons (number of MBP-positive axons)/(total number of axons), compared with the untreated group (85.0±0.9%), significant improvement was observed in MeCbl sheet group (91.0±0.8%) like the MeCbl pump group (91.5±0.6%).

When the sheet containing, as a drug, the present extract, NGF or BDNF was implanted, the improvement was also observed.

Figure 16:
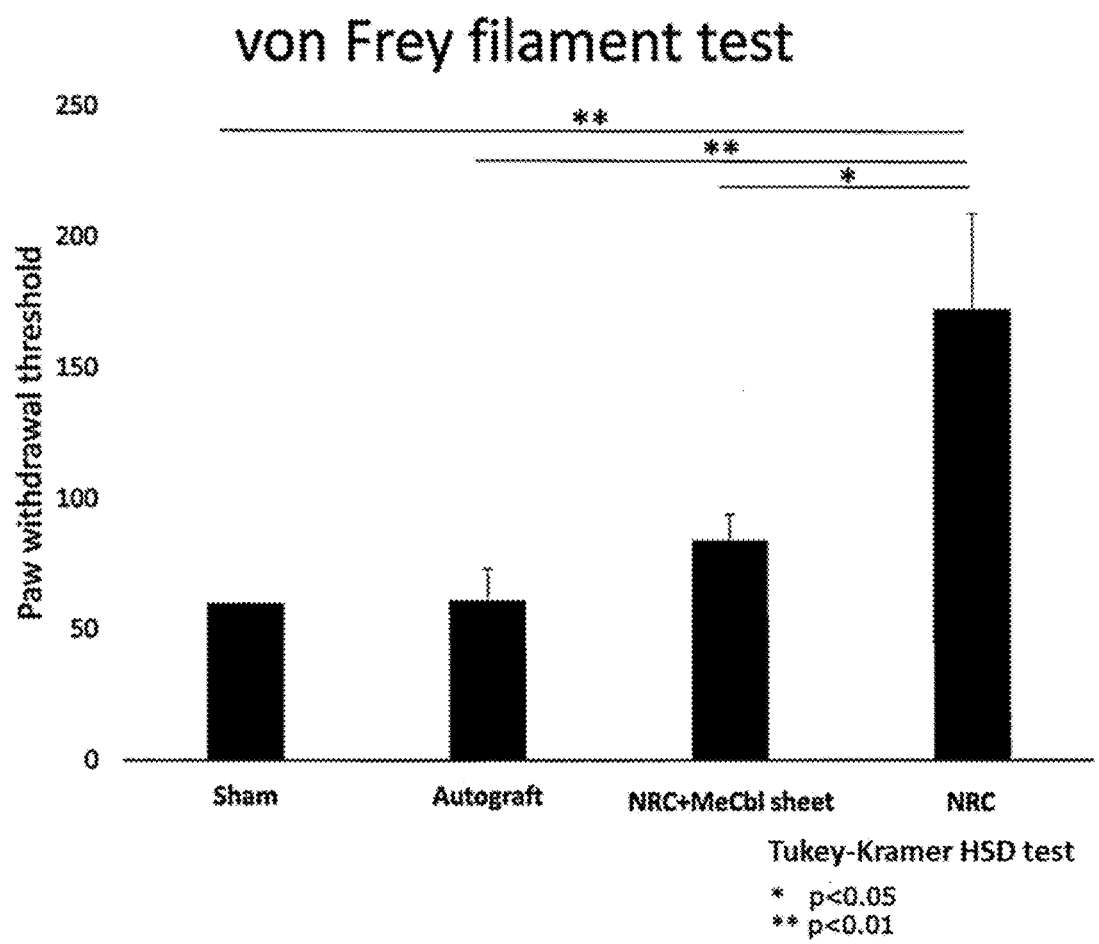
FIG. 16 illustrates the results of an experiment for evaluating the drug efficacy of the present sheet containing vitamin B12 in nerves bonded with a nerve regeneration conduits (NRC) using a rat sciatic nerve-deficient model, wherein a von Frey filament test was carried out during the 12th week after a surgery to evaluate a sensory function.

B. Evaluation of Drug Efficacy Using Rat Sciatic Nerve-Deficient Model (1) Evaluation of Sensory Function The results are shown in FIG. 16. In the von Frey filament test, compared with the artificial nerve conduit group (172.0±36.7 g), significant improvement was observed in the artificial nerve conduit+MeCbl sheet group (84.0±9.80 g).

When the sheet containing, as a drug, the present extract, NGF or BDNF was implanted, the improvement was also observed.

(2) Electrophysiological Evaluation

Figure 17:
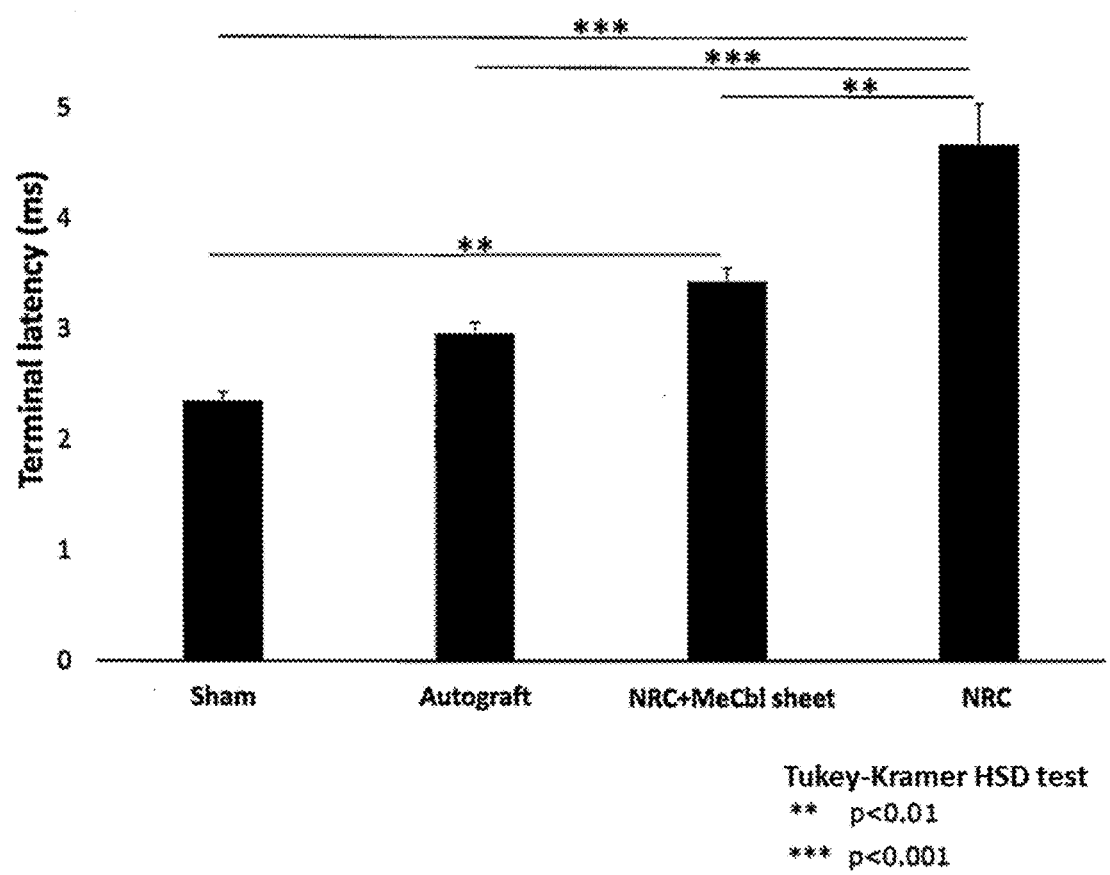
FIG. 17 illustrates the results of an experiment for evaluating the drug efficacy of the present sheet containing vitamin B12 in nerves bonded with an NRC using a rat sciatic nerve-deficient model, wherein an electrophysiological evaluation (TL) was carried out during the 12th week after a surgery.
Figure 18:
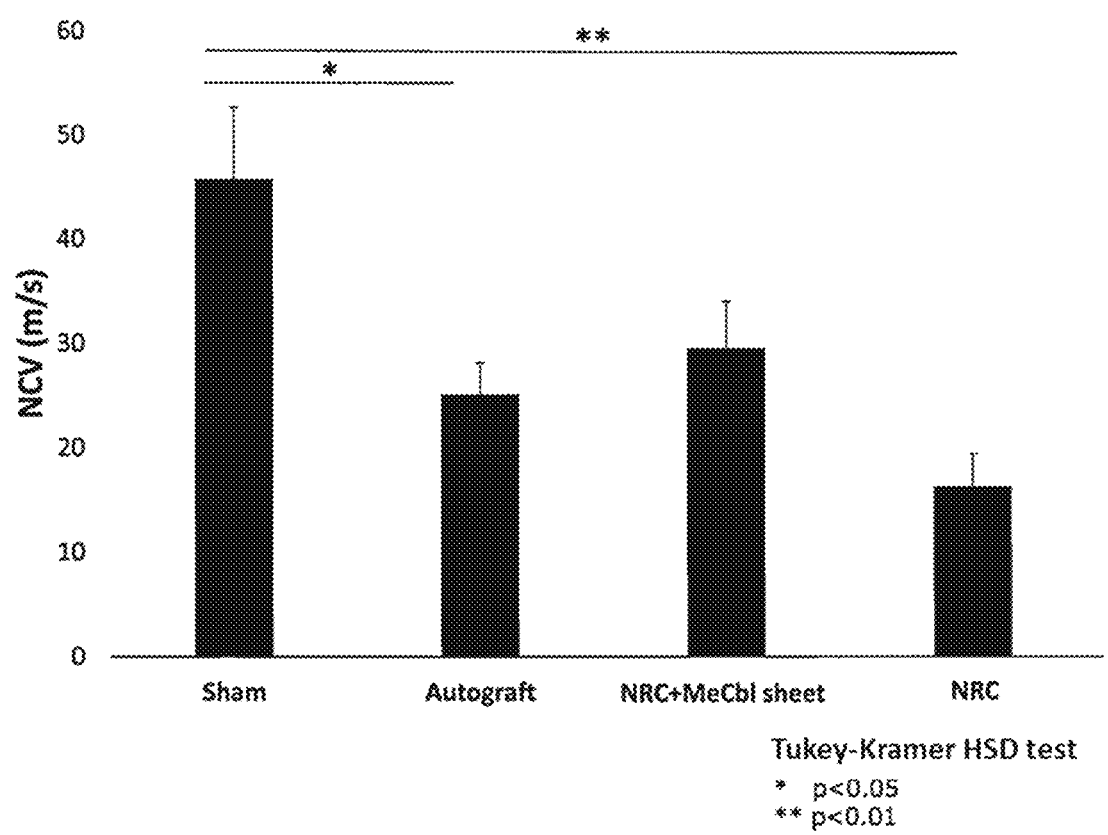
FIG. 18 illustrates the results of an experiment for evaluating the drug efficacy of the present sheet containing vitamin B12 in nerves bonded with an NRC using a rat sciatic nerve-deficient model, wherein an electrophysiological evaluation (NCV) was carried out during the 12th week after a surgery.

The results of the TLs are shown in FIG. 17, and the results of the NCVs are shown in FIG. 18. In the TLs, compared with the artificial nerve conduit group (4.67±0.37 m/s), improvement was observed in the artificial nerve conduit+MeCbl sheet group (3.43±0.12 m/s). In the NCVs, compared with the artificial nerve conduit group (16.3±3.13 m/s), an improvement tendency was observed in the nerve regeneration conduit+MeCbl sheet group (29.5±4.50 m/s).

When the sheet containing, as a drug, the present extract, NGF or BDNF was implanted, the improvement was also observed.

(3) Histological Evaluation

With respect to the number of regenerated axons per sq. mm and the ratio of myelinated axons (number of MBP-positive axons)/(total number of axons), improvement was observed in the artificial nerve conduit+MeCbl sheet group compared with the artificial nerve conduit group.

When the sheet containing, as a drug, the present extract, NGF or BDNF was implanted, the improvement was also observed.

When the drug-containing sheet was implanted into a nerve injury site topically, the enhancement of recovery after nerve injury was observed without the need to increase the concentration of the drug in the blood. That is, the recovery of a motor function, a sensory function and an electrophysiological function after nerve injury was observed, and the improvement in a gait analysis was also observed. Furthermore, from the histological viewpoint, the increase in the number of myelinated axons was observed. As mentioned above, the present invention is very useful for the recovery of functions after peripheral nerve injury.

The present invention is not to be limited by the above-mentioned embodiments and examples, and various changes may be made within the scope described in the claims Embodiments obtained by combining technical means respectively disclosed in different embodiments as appropriate are also included within the technical scope of the present invention. All of the academic literatures and patent documents cited in the description are incorporated herein by reference.

The invention claimed is:

1. A sustained drug release sheet comprising a non-woven fabric that is formed from nanofibers containing vitamin B12 in the absence of GDF-5 or GDF-5-related proteins for treating nerve injury and a biocompatible polymer,
    wherein the vitamin B12 is distributed inside the nanofibers,
    a content of vitamin B12 in the sustained drug release sheet is in a range of 1 to 30% by weight,
    the biocompatible polymer is at least one biodegradable aliphatic polyester selected from the group consisting of polycaprolactone or a copolymer thereof, polylactic acid or a copolymer thereof, and polyglycolic acid or a copolymer thereof, and
    the weight of the sheet is in a range of 1 $mg/cm^2$ to 100 $mg/cm^2$.

2. The sustained drug release sheet according to claim 1, wherein a content of vitamin B12 in the sustained drug release sheet is in a range of 1 to 10% by weight.

3. The sustained drug release sheet according to claim 1, wherein the weight of the sheet is in a range of 1 $mg/cm^2$ to 50 $mg/cm^2$.

4. The sustained drug release sheet according to claim 1, wherein the weight of the sheet is in a range of 1 $mg/cm^2$ to 10 $mg/cm^2$.

5. A sustained drug release sheet comprising a non-woven fabric that is formed from nanofibers containing a drug for treating nerve injury and a biocompatible polymer,
    wherein the drug consists of vitamin B12,
    the vitamin B12 is distributed inside the nanofibers,
    the vitamin B12 is a sole effective ingredient for treating the nerve injury,
    a content of vitamin B12 in the sustained drug release sheet is in a range of 1 to 30% by weight,
    the biocompatible polymer is at least one biodegradable aliphatic polyester selected from the group consisting of polycaprolactone or a copolymer thereof, polylactic acid or a copolymer thereof, and polyglycolic acid or a copolymer thereof, and
    the weight of the sheet is in a range of 1 $mg/cm^2$ to 100 $mg/cm^2$.

6. The sustained drug release sheet according to claim 5, wherein the content of vitamin B12 in the sustained drug release sheet is 1 to 10% by weight.

7. The sustained drug release sheet according to claim 5, wherein the weight of the sheet is in a range of 1 $mg/cm^2$ to 50 $mg/cm^2$.

8. The sustained drug release sheet according to claim 5, wherein the weight of the sheet is in a range of 1 $mg/cm^2$ to 10 $mg/cm^2$.

* * * * *